United States Patent
Chan et al.

(10) Patent No.: US 12,322,485 B2
(45) Date of Patent: Jun. 3, 2025

(54) INHALER SYSTEM

(71) Applicant: Norton (Waterford) Limited, Waterford (IE)

(72) Inventors: Eric Chan, Cambridge, MA (US); John Macey, Cambridge, MA (US); Jon Cody Goldberg, Cambridge, MA (US); Jenna-Leigh Meola, Boston, MA (US)

(73) Assignee: Norton (Waterford) Limited, Waterford (IE)

( * ) Notice: Subject to any disclaimer, the term of this patent is extended or adjusted under 35 U.S.C. 154(b) by 720 days.

(21) Appl. No.: 17/366,634

(22) Filed: Jul. 2, 2021

(65) Prior Publication Data
US 2022/0005573 A1    Jan. 6, 2022

Related U.S. Application Data

(60) Provisional application No. 63/047,680, filed on Jul. 2, 2020.

(51) Int. Cl.
*G06F 11/30* (2006.01)
*A61M 15/00* (2006.01)
*G16H 20/13* (2018.01)

(52) U.S. Cl.
CPC ........ *G16H 20/13* (2018.01); *A61M 15/0001* (2014.02); *A61M 15/008* (2014.02); *A61M 2205/502* (2013.01); *A61M 2205/52* (2013.01)

(58) Field of Classification Search
CPC ..................................................... G16H 20/13
See application file for complete search history.

(56) References Cited

U.S. PATENT DOCUMENTS

2010/0250280 A1*  9/2010  Sutherland .......... A61M 15/008
                                                    726/4
2017/0169184 A1   6/2017  Doswell et al.

FOREIGN PATENT DOCUMENTS

GB        2552539      *   1/2018
GB        2552539 A        1/2018
WO     2014033229 A1       3/2014

OTHER PUBLICATIONS

Greene, Garrett , et al., "A Novel Statistical Method for Assessing Effective Adherence to Medication and Calculating Optimal Drug Dosages", PLOS ONE, vol. 13, No. 4; https://doi.org/10.1371/journal.pone.0195663, Apr. 20, 2018, 17 Pages.

(Continued)

*Primary Examiner* — Phuong Huynh
(74) *Attorney, Agent, or Firm* — Flaster Greenberg P.C.

(57) ABSTRACT

A system may include a plurality of inhalers, where each inhaler comprising medicament, a processor, memory, and a transmitter, multiple processing modules that may reside at least partially on a user device, a digital health platform (DHP) that is configured to receive and aggregate inhaler data from inhalers that are associated with a plurality of different users and a plurality of different medicament types. The DHP may determine a subset of the usage events based on the determined medication type, the determined time of day, and/or the determined date range. The DHP may determine a filtered list of users out of the plurality of users based on a comparison of the selected inhalation count threshold with the number of usage events that are associated with the same user and medication type.

23 Claims, 12 Drawing Sheets

(56) References Cited

OTHER PUBLICATIONS

Colthorpe, Paul, et al., "Adding Electronics to the Breezhaler: Satisfying the Needs of Patients and Regulators", Respiratory Drug Delivery 2018, vol. 1, 2018: 71-80.

* cited by examiner

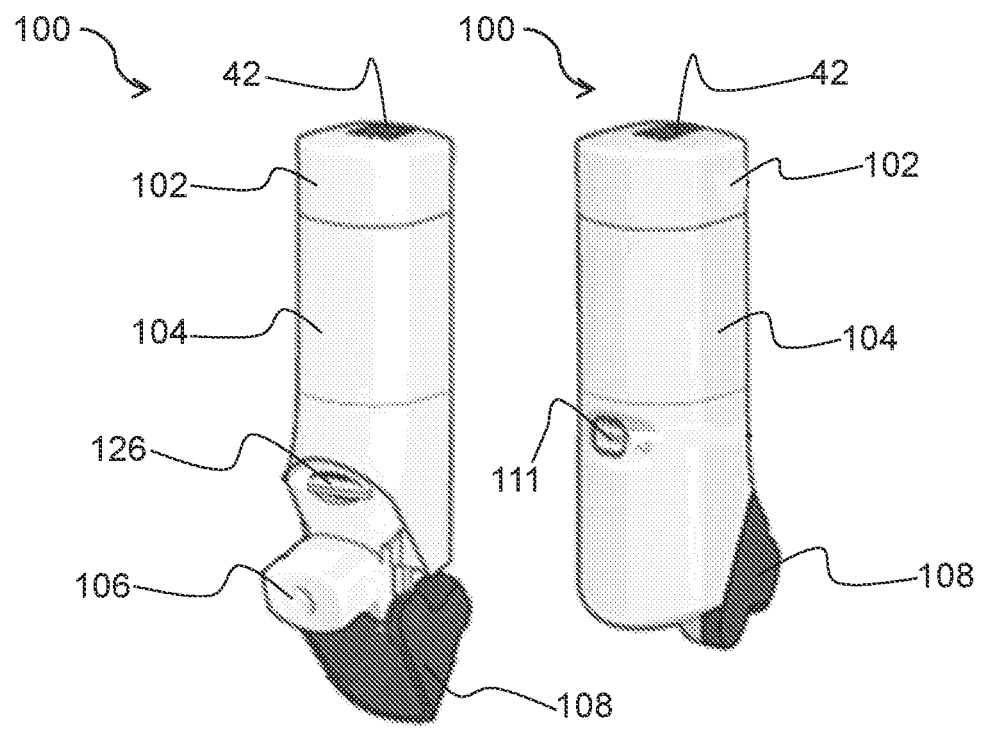
FIG. 4
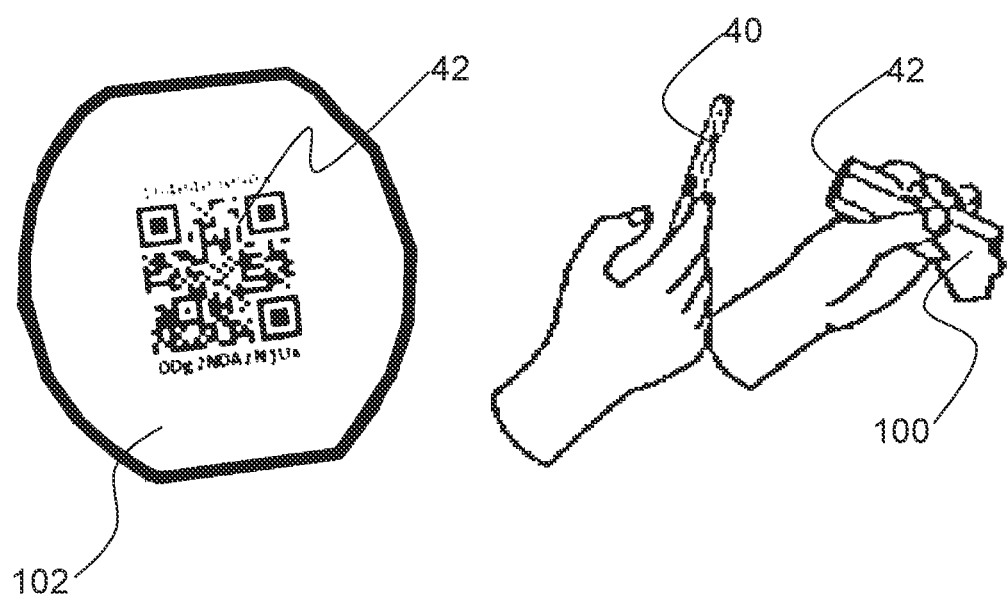
FIG. 5
FIG. 6

INHALER SYSTEM

CROSS-REFERENCE TO RELATED APPLICATIONS

This application claims priority to U.S. patent application No. 63/047,680, filed Jul. 2, 2020, which are incorporated herein by reference in its entirety.

BACKGROUND

Drug delivery devices facilitate the delivery of medication into a patient's body via various routes of administration. Typical routes of administration include oral, topical, sublingual inhalation, injection, and the like. The devices may be used to deliver medications for the treatment various diseases, ailments, and medical conditions. Inhalation devices, for example, may be used to treat asthma, chronic obstructive pulmonary disease (COPD) and/or cystic fibrosis (CF). While drug delivery devices are designed to deliver an appropriate dose of medication to a patient as part of a therapeutic treatment, the effectiveness of a particular treatment may be influenced by non-physiological factors, such as the patient's adherence and compliance.

In the context of a drug therapy, adherence may refer to the degree to which a patient is following a prescribed dosing regimen. For example, if the patient's prescription calls for two doses each day, and the patient is taking two doses per day, the patient may be considered 100% adherent. If the patient is only taking one dose per day, he or she may be deemed only 50% adherent. In the latter case, the patient may not be receiving the treatment prescribed by his or her doctor, which may negatively affect the efficacy of the therapeutic treatment.

Compliance may refer to a patient's technique when using a particular drug delivery device. If the patient is using the device in a manner that is recommended by a doctor or by a manufacturer, the device is likely to deliver the desired dose of medication and the patient may be deemed compliant. However, if the device is not being used properly during drug administration, the device's ability to deliver a proper dose of medication may be compromised. As such, the patient may be deemed non-compliant. In the case of an inhalation device, for example, the patient may need to achieve a minimum inspiratory effort to ensure a full dose of medication is delivered from the device into the patient's lungs. For some patients, such as children and the elderly, meeting the requirements for full compliance may be difficult, for example, due to physical limitations, such as limited lung function. Accordingly, like adherence, failing to achieve full compliance may reduce the effectiveness of a prescribed treatment.

A patient's ability to achieve full compliance may be further complicated by certain physical properties of the medication. For example, some respiratory medications may consist of fine particles and/or may lack any odor or taste. Thus, a patient using an inhalation device may not be able to correct a non-compliant use because he or she may not be able to immediately detect or sense that medication is being inhaled and/or know whether the amount of inhaled medication complies with the prescription.

Further, many respiratory diseases, such as asthma and COPD, are life-long conditions where treatment involves the long-term administration of medicaments to manage the patients' symptoms and to decrease the risks of irreversible changes. There is currently no cure for diseases like asthma and COPD. Treatment takes two forms. First, a maintenance aspect of the treatment is intended to reduce airway inflammation and, consequently, control symptoms in the future. The maintenance therapy is typically provided by inhaled corticosteroids, alone or in combination with long-acting bronchodilators and/or muscarinic antagonists. Secondly, there is also a rescue (or reliever) aspect of the therapy, where patients are given rapid-acting bronchodilators to relieve acute episodes of wheezing, coughing, chest tightness and shortness of breath.

Sufferers of respiratory diseases may thus be prescribed more than one medication, such as more than one inhaled medication, for controlling their symptoms. The sufferer may alternatively or additionally make use of a plurality of inhalers, each being used at different times/locations, which all deliver the same inhaled medicament. There is a growing desire to monitor administration of such medicaments in ways which are reliable, and convenient from the point of view of the sufferer. Further, such monitoring is also desirable for the patient's health care provider, who requires a simple and cohesive manner to assess each patient's adherence and compliance, and view data that indicates the highest risk of exacerbation or indicates that the patient's treatment regimen should be altered.

SUMMARY

A system may include a plurality of inhalers, where each inhaler comprises medicament, a processor, memory, and a transmitter. Each inhaler is configured to determine usage events of the inhaler caused by a subject, such as an inhalation event (e.g., as detected by a sensor, such as a pressure sensor or acoustic sensor) or an operation, such as the opening of a mouthpiece cover, the actuation of a switch (e.g., that is used to prime a dose of the medicament), or the detection of a particular movement of the inhaler, like shaking (e.g., as detected using an accelerometer). The inhaler may assign a time to each usage event. The inhaler is also configured to send the data indicating the usage events and the time of the usage events to another device, which in some examples is a mobile application residing on a user device. Although described as inhalers, in some examples, the system may include other medical devices in addition to or as an alternative to inhalers. Further, in some examples, the system may include smart add-on devices that include a processing module and/or a transmission module (e.g., a processor, memory, and transmitter) that are configured to attach to otherwise "dumb" inhalers instead of, or in addition to, including inhalers described herein that include a processing module and/or a transmission module (e.g., a processor, memory, and transmitter).

The system may also include a processing module that is configured to connect to, receive, and aggregate inhaler data from inhalers that are associated with a plurality of different users and a plurality of different medicament types, such as one or more rescue medicament types and/or one or more maintenance medicament types. In some examples, the rescue medicament type is albuterol (such as albuterol sulfate), and the maintenance medicament type is fluticasone (such as fluticasone propionate or fluticasone furoate) or salmeterol (such as salmeterol xinafoate) combined with fluticasone (such as fluticasone propionate or fluticasone furoate). This processing module may be referred to as a digital health platform (DHP), as will be described in more detail below. The DHP may include or be associated with a transceiver, memory, and a processor. For instance, the DHP may reside on one or more servers.

The DHP is configured to receive data relating to usage events and a time of each of the usage events (e.g., a time stamp for the usage event) for a plurality of inhalers, where the inhalers are associated with a plurality of different users. Each inhaler is associated with at least one user and one of a rescue medicament type or a maintenance medicament type. In some examples, the system may include mobile applications that are residing on user devices (e.g., such as a smartphone or tablet), and the DHP may receive the usage events and time stamps for the plurality of inhalers through a mobile application that resides on a user device (e.g., such as a smartphone or tablet). However, in other examples, the DHP may receive the usage events and time stamps directly from the inhalers themselves, for example, in instances where the inhalers include a cellular chipset that allows the inhalers to transmit the usage events and time stamps to the DHP.

The DHP is configured to determine the medicament type and the user associated with each of the plurality of inhalers (e.g., and in turn each usage event). In some examples, this is performed at a mobile application residing on the user's device, and then sent to the DHP along with the usage data and associated timestamp. In other examples, the DHP determines the medicament type and user associated with each inhaler.

The DHP is configured to determine a subset of the plurality of inhalers that are part of a program out of a plurality of programs. A program defines a set of criteria, such as types of medications (e.g., any combination of rescue and/or maintenance medications), specific patients and in turn their applicable inhalers (e.g., based on medication type), other users of the programs such as particular physicians, practice groups, and/or administrators, the types of data presented to the health care provider such as charts, event tables, usage summaries, etc. The DHP (e.g., via a health care provider) may configure and establish any number of programs. Further, a particular patient and any combination of their inhalers may be associated with any number of unique programs. Therefore, although the DHP may include data from any number of inhalers associated with any number of users, a program may be limited to a subset of the available inhalers and/or users.

The DHP may be configured to generate a reduced (e.g., filtered) list of users based on the plurality of usage events and one or more variables. For example, the DHP may determine a medication type(s), a time of day, and/or a date range. In some examples, the DHP may receive a selection (e.g., from a user) of a medication type(s), a time of day, and/or a date range. The medication type(s) may include one or more rescue medication types and/or one or more maintenance medication types. The time of day may include, for example, daytime (e.g., defined as between 8 am and 8 pm), nighttime (e.g., defined as between 8 pm and 8 am), and/or all day. Alternatively or additionally, time of day may include a customizable definition of a time period, such as between a start time (e.g., 10 pm) and an end time (e.g., 6 am). The date range may include a start and end date, or may include a selection of a preconfigured, dynamically adjusted date range, such as the last week(s), last month, etc.

The DHP may determine a subset of the usage events based on the determined medication type, the determined time of day, and/or the determined date range. For example, the DHP may apply a usage event filter to filter the plurality of usage events received from a plurality of different inhalers to determine a subset of usage events based on the determined medication type, the determined time of day, and/or the determined date range.

The DHP may determine an inhalation count threshold. For example, the DHP may receive a selection of the inhalation count threshold, for instance, from a user. The inhalation count threshold may be a number. The DHP may determine a number of usage events out of the subset of usage events that are associated with the same user and medication type. For example, the DHP may associate (e.g., group or combine) usage events out of the subset of usage events that have a common user and medication type. The DHP may determine a filtered list of users out of the plurality of users based on a comparison of the selected inhalation count threshold with the number of usage events that are associated with the same user and medication type. For example, the DHP may apply an inhalation count threshold filter to generate the filtered list of users. For instance, the DHP may compare the combined usage events that have the common user and medication type to the inhalation count threshold and a criteria (e.g., less than, greater than, less than or equal to, greater than or equal to, etc.). If the combined usage events do meet the inhalation count threshold and criteria (e.g., are great than, or, alternatively are less than the inhalation count threshold), the DHP may include the user associated with the combined usage events in the filtered list of users. However, if the combined usage events do not meet the inhalation count threshold and the criteria, the DHP may ignore (e.g., discard) the user associated with the combined usage events. The DHP may generate a graphical user interface (GUI) (e.g., via a display device of a remote computer terminal) that comprises the number of usage events for each user of the filtered list of users.

Further, in some examples, the DHP may be configured to store a filter based on the determined medication type, the determined time of day, the determined date range, the selected inhalation count threshold, and/or the criteria. The DHP may associate the filter with the program so that the filter may be selected by a plurality of different heath care providers who are associated with an organization and the program. Further, in some examples, the DHP may be configured to apply the filter to other programs associated with the organization and/or outside of the organization.

The DHP may receive a plurality of usage events, where each usage event includes inhalation data from an inhaler of a particular medication for a user. The DHP may determine a subset of the usage events based on a comparison of a first inhalation metric of the usage events to one or more thresholds, and categorize the subset of usage events based on a second inhalation metric. For example, the DHP may compare the first inhalation metric of each usage event (e.g., a peak inspiratory flow (PIF) of each usage event) to one or more thresholds, such as an upper threshold and/or a lower threshold, to determine a subset of usage events. The upper and/or lower thresholds may be indicative of a valid inhalation occurring during the usage event. The DHP may categorize the subset of usage events (e.g., after the comparison of the first inhalation to one or more thresholds) between an upper value and a lower value for the second inhalation metric (e.g., between 0.3 L and 6 L in the example of inhalation volume). In some instances, the DHP may generate a GUI (e.g., via a display device of a remote computer terminal) that comprises the subset of usage events and the associated second inhalation metric for each of the subset of usage events. The GUI may include a scatter chart of the subset of usage events and the associated second inhalation metric for each. The GUI may include a trend line across the subset of usage events, where for instance, the DHP may determine the trend line using a LOESS (Locally Estimated Scatterplot Smoothing) algorithm with a smoothing factor (e.g., a smoothing factor of 0.5).

In some example, the DHP may determine the subset of the usage events by comparing the first inhalation metric to a lower threshold and an upper threshold, wherein the subset of usage events are those usage events where the first inhalation metric is between the lower threshold and the upper threshold. The first inhalation metric may, for example, be a peak inhalation flow (PIF) of the usage event, and the second inhalation metric may be the inhalation volume of the usage event. For instance, if the second inhalation metric comprises inhalation volume, then the DHP may categorize the subset of inhalation metrics between an upper value associated with the second inhalation metric (e.g., 6 L) and a lower value associated with the second inhalation metric (0.3 L).

The DHP is configured to manipulate data differently and/or generate different alerts based on the specific medications, patients, users (e.g., health care providers), and/or therapeutic devices or areas defined by the program. As one example, the DHP may be configured to generate a first type of alert when a rescue medicament type and one or more maintenance medicament types are included in the program, but generate a second type of alert when the rescue medicament type is not included in the program. For instance, the DHP may be configured to generate a first alert that indicates a prioritized listing of users with the highest number of usage events (e.g., over a particular time range, such as one week) of inhalers that include a rescue medicament type when the rescue medicament type and one or more maintenance medicament types are included in the program, and generate a second alert that indicates a prioritized listing of users with the lowest number of usage events (e.g., over a particular time range, such as one month) of inhalers that include the maintenance medicament type when the rescue medicament type is not included in the program.

In some examples, the alert is provided via a display device that, for example, may reside at a health care provider's facility. In such examples, the DHP may be configured to cause the display device to present a prioritized listing of users with the highest number of usage events (e.g., over a particular time range, such as one week) of inhalers that include a rescue medicament type when the rescue medicament type and one or more maintenance medicament types are included in the program, but also be configured to present a prioritized listing of users with the lowest number of usage events (e.g., over a particular time range, such as one month) of inhalers that include the maintenance medicament type when the rescue medicament type is not included in the program. In some examples, the display device is part of a computer or server associated with (e.g., operated by) a health care provider, and the DHP is configured to cause the display device to present the prioritized listing of users by sending the computer the necessary data to present a GUI at the computer that includes the prioritized listing of users. Further, when causing the display device to present data for a program, the DHP may allocate different time ranges for usage events for different medicament types.

In some examples, the DHP is configured to determine and differentiate users that are associated with an inhaler with zero doses and a confirmed connection within a time frame as compared to users that are associated with an inhaler with zero doses without a confirmed connection within the time frame. The DHP may be configured to generate an alert that indicates those users that are associated with an inhaler with zero doses and a confirmed connection within a time frame. In some examples, the DHP may prioritize users that are associated with an inhaler with zero doses and a confirmed connection within a time frame over users that are associated with an inhaler with zero doses without a confirmed connection within the time frame. For example, the DHP may include many inhalers that have zero dosage events over a particular period of time, such as the past week or month. However, some of these inhalers may not have actually been used by a user, while other inhalers may or may not have been used, but the DHP may be unaware of the reliability of the usage data. As such, the DHP may determine a last synchronization time for each of the plurality of inhalers. The last synchronization time indicates the last time the inhaler was connected with a user device that includes a mobile application (e.g., or, alternatively, connected with the DHP). The DHP may differentiate users that are associated with an inhaler with zero doses and a last synchronization time within a time frame, such as the last week or two, from the users that are associated with an inhaler with zero doses without a last synchronization time within the time frame. The DHP may then generate an alert that indicates the users that are associated with an inhaler with zero doses and a last synchronization time within the time frame. For instance, in some examples, the DHP may cause a display device (e.g., associated with a health care provider) to present a listing of users, where the listing prioritizes users with an inhaler that has zero usage events and a confirmed connection between the inhaler and the application residing on the user device within a time frame over users with an inhaler that has zero usage events without a confirmed connection between the inhaler and the application residing on the user device within the time frame. In some examples, the inhalers all include a maintenance medicament type. For example, the program may be limited to inhalers that include a maintenance medicament type. Further, the time frame may be the last month or the last 30 days.

In some examples, the DHP may be configured to determine a last synchronization time for each of the plurality of inhalers. The last synchronization time may indicate the most recent time the inhaler was connected with an application residing on a user device (e.g., or, alternatively, connected with the DHP). The DHP may be configured to determine an all-connected duration for each medicament type associated with each user. For example, the DHP may be configured to determine a group of inhalers that are all associated with one user and that all include the same medicament. The DHP may be configured to then determine the last synchronization time for all of those inhalers. Next, the DHP may be configured to determine the oldest or least recent last synchronization time from the group and set this time as the all-connected duration for that particular medicament type for that particular user. The DHP may be configured to generate an alert that indicates the all-connected duration, the medicament type, and the user. For example, the DHP may be configured to cause a display device to present a listing of a plurality of users and an all-connected duration for each medicament type associated with each user. As noted herein, the all-connected duration may indicate the last time that all of the inhalers of a particular medication type associated with the user have a confirmed connection between the inhaler and the application residing on the user device associated with the user, for example, regardless of whether a usage event was transferred during the connection. In some examples, the all-connected duration indicates a number of hours or a number of days. In some examples, the all-connected duration indicates the oldest last synchronization time of the inhalers of the particular medication type associated with the user. It should be appreciated that at least some of the users will be associated with multiple inhalers of the same medicament type. For example, a user may have multiple inhalers that include a rescue medicament (e.g., and keep them at different locations). Further, a user may have multiple inhalers that include a maintenance medicament, such as when they are transitioning between refills.

BRIEF DESCRIPTION OF THE DRAWINGS

FIG. 4 are diagrams of front and rear views of the exterior of an example inhaler.

FIG. 5 is a diagram of an uppermost surface of the top cap of the inhaler shown in FIG. 4.

FIG. 6 is a schematic depiction of a pairing process between the inhaler shown in FIG. 4 and a user device.

DETAILED DESCRIPTION

Figure 1:
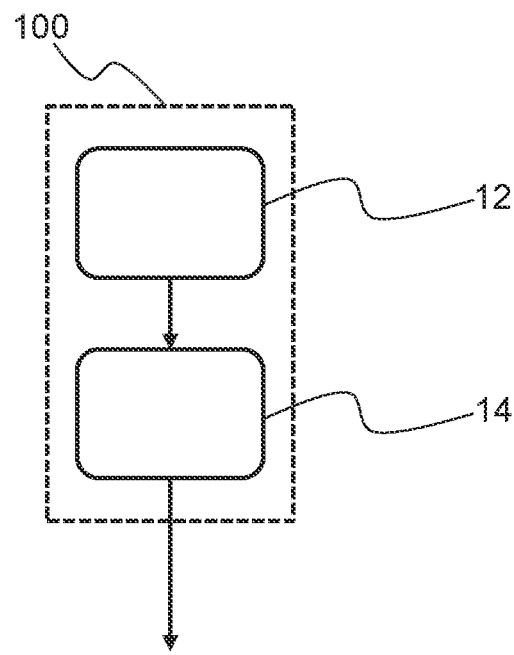
FIG. 1 is a block diagram of an example inhaler.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the figures to indicate the same or similar parts.

The present disclosure describes devices, systems and methods for sensing, tracking processing, and/or presenting usage conditions and parameters associated with a drug delivery device. The devices, systems and methods are described in the context of a breath-actuated inhalation device for delivering medication into a user's lungs. However, the described solutions are equally applicable to other drug delivery devices, such as an injector, a metered-dose inhaler, a nebulizer, a transdermal patch, or an implantable.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath.

The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate), fluticasone (propionate or furoate), mometasone (furoate), ciclesonide and dexamethasone (sodium). Parentheses indicate preferred salt or ester forms. Particular mention should be made of budesonide, beclomethasone and fluticasone, especially budesonide, beclomethasone dipropionate, fluticasone propionate and fluticasone furoate.

Different classes of bronchodilators target different receptors in the airways. Two commonly used classes are β2-agonists and anticholinergics.

β2-Adrenergic agonists (or "β2-agonists") act upon the β2-adrenoceptors which induces smooth muscle relaxation, resulting in dilation of the bronchial passages. They tend to be categorised by duration of action. Examples of long-acting β2-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Examples of short-acting β2-agonists (SABA) are albuterol (sulfate) and terbutaline (sulfate). Particular mention should be made of formoterol, salmeterol, indacaterol and vilanterol, especially formoterol fumarate, salmeterol xinafoate, indacaterol maleate and vilanterol triphenylacetate.

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate) or beclomethasone (dipropionate)-formoterol (fumarate). Thus, the rescue medicine is preferably a SABA or a rapid-acting LABA, more preferably albuterol (sulfate) or formoterol (fumarate), and most preferably albuterol (sulfate).

Anticholinergics (or "antimuscarinics") block the neurotransmitter acetylcholine by selectively blocking its receptor in nerve cells. On topical application, anticholinergics act predominantly on the M3 muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), umeclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide). Particular mention should be made of tiotropium, aclidinium, umeclidinium and glycopyrronium, especially tiotropium bromide, aclidinium bromide, umeclidinium bromide and glycopyrronium bromide.

A number of approaches have been taken in preparing and formulating these medicaments for delivery by inhalation, such as via a dry powder inhaler (DPI), a pressurized metered dose inhaler (pMDI) or a nebulizer.

According to the GINA (Global Initiative for Asthma) Guidelines, a step-wise approach is taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localised to the airways, lung parenchyma and pulmonary vasculature. Phenotypically, these changes reduce the healthy ability of the lungs to absorb and expel gases.

Bronchitis is characterised by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting $\beta 2$-agonists and corticosteroids. The medicaments are often administered as a single therapy or as combination treatments.

Patients are categorised by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prn or a short-acting $\beta 2$-aginist (SABA) prn. Patient group B are recommended a long-acting muscarinic antagonist (LAMA) or a long-acting $\beta 2$-aginist (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization). An exacerbation within the meaning of the present disclosure includes both moderate and severe exacerbations.

Provided is a system comprising at least one first inhaler which delivers a first medicament to a subject. One or more (or each) of the at least one first inhaler comprises a first use determination system configured to determine a first value of a usage parameter relating to use of the respective first inhaler. One or more (or each) of the at least one inhaler also comprises a first transmission module configured to encrypt first data based on the first value, and transmit the encrypted first data. The system further comprises at least one second inhaler which delivers a second medicament to the subject. The second medicament is different from the first medicament. One or more (or each) of the at least one second inhaler comprises a second use determination system configured to determine a second value of a usage parameter relating to use of the respective second inhaler, and a second transmission module configured to encrypt second data based on the second value, and transmit the encrypted second data.

The system includes at least one processing module, which for example, may reside on an external device (e.g., a user device, such as a smartphone, tablet, or personal computer, or external server). The processing module receives the first encrypted data and the second encrypted data, and distinguishes between the first encrypted data and the second encrypted data. The processing module determines first usage information relating to the first medicament from the distinguished first encrypted data, and determines second usage information relating to the second medicament from the distinguished second encrypted data. The processing module may control a user interface to communicate the first and second usage information.

One or more (or each) of the at least one first inhaler is configured to deliver a first medicament to a subject. One or more (or each) of the at least one first inhaler may, for example, comprise a first medicament reservoir containing the first medicament.

The system also comprises at least one second inhaler. One or more (or each) of the at least one second inhaler is configured to deliver a second medicament to the subject. This may be, for example, the same subject to whom the first medicament is administered via the first inhaler. The first medicament is different from the second medicament. One or more (or each) of the at least one second inhaler may, for example, comprise a second medicament reservoir containing the second medicament.

In a non-limiting example, the first medicament is a rescue medicament for use by the subject as needed, and the second medicament is a maintenance medicament which is used by the subject according to a predetermined treatment regimen.

The rescue medicament is as defined hereinabove and is typically a SABA or a rapid-onset LABA, such as formoterol (fumarate). The rescue medicament may also be in the form of a combination product, e.g. ICS-formoterol (fumarate), typically budesonide-formoterol (fumarate) or beclomethasone (dipropionate)-formoterol (fumarate). Such an approach is termed "MART" (maintenance and rescue therapy).

In a non-limiting example, the first medicament is albuterol (sulfate), and the second medicament is fluticasone (propionate or furoate), or salmeterol (xinafoate) combined with fluticasone (propionate or furoate).

More generally, the first medicament and the second medicament (and any further medicaments included in any further inhalers included in the system) may comprise any suitable active pharmaceutical ingredient. Thus, any class of medication may be delivered by, in other words housed within, the inhalers included in the system. The system permits consolidated handling and communicating of usage information irrespective of the particular medications which are delivered by the inhalers.

One or more (or each) of the at least one first inhaler comprises a first use determination system. The first use determination system is configured to determine a first value of a usage parameter relating to use of the respective first inhaler. The usage parameter may, for instance, comprise a use of, such as an inhalation of the first medicament performed by the subject using, the respective first inhaler. Alternatively or additionally, the usage parameter may comprise a parameter relating to airflow during inhalation of the first medicament performed by the subject.

Similarly, one or more (or each) of the at least one second inhaler comprises a second use determination system. The second use determination system is configured to determine a second value of a usage parameter relating to use of the respective second inhaler. In the case of the second inhaler, the usage parameter may, for instance, comprise a use of, such as an inhalation of the second medicament performed by the subject using, the respective second inhaler. Alternatively or additionally, the usage parameter may comprise a parameter relating to airflow during inhalation of the second medicament performed by the subject.

One or more (or each) of the first inhaler comprises a first transmission module configured to encrypt first data based on the first value, and transmit the encrypted first data. Similarly, one or more (or each) of the second inhaler comprises a second transmission module configured to encrypt second data based on the second value, and transmit the encrypted second data.

The first and second transmission modules may each include an encryption device capable of encrypting the first and second data, respectively. For example, the encryption device may be implemented using hardware such a digital signal processor (DSP), a microcontroller, a processor, and/or the like. The encryption device may be incorporated into other portions of the first and/or second transmission modules, such as a transceiver use to transmit the encrypted data. Examples of different types of transceivers are described in more detail below.

Further, it should be appreciated that in some examples, the system may include smart add-on devices that include a processing module and/or a transmission module (e.g., a processor, memory, and transmitter) that are configured to attach to otherwise "dumb" inhalers instead of, or in addition to, including the inhalers that are described herein.

The system comprises at least one processing module configured to receive the first encrypted data and the second encrypted data from the respective transmission modules (e.g., directly or indirectly, for example, via an intermediate device).

The processing module may include a general purpose processor, a special purpose processor, a DSP, a microcontroller, an integrated circuit, and/or the like that may be configured using hardware and/or software to perform the functions described herein for the processing module. The processing module may include a power supply and/or a battery. In some examples, the processing module may reside partially or entirely on any combination of one or more user devices (e.g., a smartphone, tablet, or personal computers) and/or remote servers. Further, in some examples, the processing module may be a patient-facing mobile application, for example, in combination with a processor or controller configured to perform the functions described herein.

Encryption of the first and second data in this manner enables transmission of the respective usage parameter values. The encryption may, for instance, further enable such transmission to be effected securely, since decryption of the respective data is implemented by the processing module configured to receive the encrypted data from the respective transmission modules. The processing module may, for example, be paired to the respective transmission modules such that the processing module is configured, e.g. exclusively configured, to decrypt the encrypted data. Thus, such encryption may enable secure transmission of the respective usage parameter values to the processing module, which secure transmission may be preferred in the context of transmission of medical data relating to inhaler usage.

In a non-limiting example, the first and/or second transmission modules are configured to transmit the respective encrypted data wirelessly. A transceiver configured to implement any suitable wireless transmission protocol may be included in the respective transmission modules, such as via Wi-Fi, Wi-MAX, Bluetooth®, Bluetooth® Smart, ZigBee, near field communication (NFC), cellular communication, television white space (TVWS) communication, or any combination thereof.

Although examples described herein may refer to a transceiver, the transceiver may be configured to transmit, but not receive, data (e.g., a transmitter but not a receiver). The transceiver may include one or more semiconductor chips, integrated circuits, and/or the like configured to implement the logic and procedures of the communication protocol. The transceiver may include radio frequency (RF) hardware such as amplifier(s), oscillator(s), modulator circuit(s), antenna(s), antenna tuner(s), and/or the like in order to transmit signals wirelessly using the communication protocol. The RF hardware may be implemented in whole or in part on the semiconductor chip(s), integrated circuit(s), and/or the like configured to implement the logic and procedures of the communication protocol.

Whilst the respective transmission modules are configured to transmit the encrypted data, in some non-limiting examples the respective transmission modules are further configured to receive data, for example from the processing module to which the encrypted data is sent. In such examples, the respective transmission modules may be regarded as a transceiver, in other words as a transmitting and receiving module.

A clock module may, for example, be included in one or more (or each) of the respective inhalers for assigning a time, for example a time stamp, to the usage parameter of the respective inhaler. The clock module may be implemented via a processor or other type of integrated circuit. The processing module may be configured to synchronize the clock modules of the respective inhalers. One or more (or each) of the respective clock modules may, for instance, receive time data transmitted from the processing module, e.g. via the respective transmission module. Such synchronization may, for instance, provide a point of reference which enables the relative timing of use of the respective inhalers to be determined, which may have clinical relevance. For example, failure to inhale a maintenance medicament during a particular time period in which such an inhalation was or such inhalations were scheduled according to a treatment regimen may be correlated with increased rescue medicament usage towards the end of, or subsequently to, that time period of non-adherence to the treatment regimen. Such diagnostic analysis may be possible when the clock modules of the respective inhalers are synchronized with each other.

Further, it should be appreciated that in some examples, the clock module of an inhaler may operate as an internal counter. When operating as an internal counter, the clock module may provide a relative count (e.g., as opposed to providing a mean solar time, such as a local mean time). For instance, the use determination system of an inhaler may start an internal counter (e.g., which counts up from 0 indefinitely) when, for example, the use determination system is woken out of an energy-saving sleep mode for the first time (e.g., after the mouthpiece cover is opened for the first time). Thereafter, any time-and-date stamp generated by the use determination system may be a relative time (or count) based on the internal counter of the clock module. The use determination system may periodically update the system clock every 250 microseconds (µs).

The processing module may, in some examples, comprise a further clock module. The clock modules of each of the respective inhalers may thus be synchronized according to the time provided by the further clock module. The further clock module may, for instance, receive the time of the time zone in which the processing module is situated. The processing module may, for example, transmit the time of the time zone to the respective clock modules, thereby to permit the clock modules to be synchronized according to the time in which the subject and their respective inhalers are located. Time stamping of the respective usage information may thus correspond to the time of day or night at the subject's geographical location. This is particularly advantageous given the relevance of, for example, night time rescue medicament use to the risk of an impending respiratory disease exacerbation. The system may thus, for example, monitor the day time and night time rescue inhaler usage of a subject who has travelled across time zones. Alternatively or additionally, reminders issued by the system to remind the subject to administer a maintenance medicament may account for the time of day or night at the subject's location.

The processing module is configured to distinguish between the first encrypted data and the second encrypted data. First usage information relating to the first medicament is determined by the processing module based on the distinguished first encrypted data. Similarly, second usage information relating to the second medicament is determined by the processing module based on the distinguished second encrypted data.

In an example, the processing module receives a first identifier assigned to the first medicament. In such an example, a second identifier is assigned to the second medicament. In such an example, the first identifier is not associated with or assigned to the second medicament and the second identifier is not associated with or assigned to the first medicament. The processing module receives the respective identifiers, and uses the respective identifiers to distinguish between the first encrypted data and the second encrypted data.

The respective identifier may, in certain examples, also denote further information, such as the dose strength of each dose delivered by the respective inhaler, for example via a suitable dose metering assembly included in the inhaler. Alternatively or additionally, the respective identifier may denote the total number of doses of the respective medicament contained by the respective inhaler (prior to first use), in other words in the medicament reservoir of the respective inhaler as supplied.

The processing module may, for instance, be accordingly configured to recognize the dose strength and/or the total number of doses which can be provided by the respective inhaler from the respective identifier. Moreover, when the respective identifier denotes the dose strength, the processing module may be configured to, for example, control the user interface to issue a notification that the label recommended dosages have been exceeded based on the respective usage information, in this case uses of the respective inhaler, and the respective dose strength.

In some examples in which a further inhaler configured for dispensing a medicament is added to the system which already includes an existing inhaler which dispenses the same medicament, the processing module may be configured to determine, based on the respective identifiers for the existing inhaler and the further inhaler whether the dose strength of the further inhaler is the same as or different from that of the existing inhaler. If the respective dose strengths are different from each other, the processing module controls a user interface to issue at least one notification. The at least one notification may, for example, comprise a notification informing the subject that the dose strength of the further inhaler is different from that of the existing inhaler and/or a notification to request that the subject discards the existing inhaler. In this manner, the system may assist the subject to adjust to a prescription change. The medicament in this example may be a rescue medicament or a maintenance medicament.

When the respective identifier denotes the total number of doses contained by the respective inhaler, the processing module may be configured to control the user interface to issue a notification that the respective inhaler should be replaced based on the respective usage information, in this case uses of the respective inhaler, and the respective total number of doses as denoted by the respective identifier. For instance, subtraction of the number of uses of the respective inhaler as determined via the use determination system from the total number of doses denoted by the respective identifier will provide the number of doses remaining in the respective inhaler. The notification may be triggered by the processing module when the determined number of doses remaining in the respective inhaler reaches or becomes lower than a predetermined threshold number of doses.

In a non-limiting example, the first identifier is included in a first key which is used to pair the first inhaler and the processing module. The processing module is configured to identify the first inhaler as an inhaler which delivers the first medicament on the basis of the first identifier included in the first key. Similarly, the second identifier may be included in a second key for pairing the second inhaler and the processing module, and the processing module identifies the second inhaler as an inhaler which delivers the second medicament on the basis of the second identifier included in the second key. In this manner, the first encrypted data is linked to the first medicament, and the second encrypted data is linked to the second medicament.

More generally, by the processing module distinguishing between the first encrypted data and the second encrypted data, the first encrypted data relating to administering of the first medicament is processed separately from the second encrypted data relating to administering of the second medicament. Because the first and second medicaments are different from each other, and thus may each be associated, for instance, with distinct treatment regimens and/or administration protocols, this separate data processing may advantageously ensure that the first usage information relating to the first medicament does not become conflated with the second usage information relating to the second medicament. The system nevertheless permits consolidated handling and communicating of the first and second usage information.

In some examples, the processing module is configured to control the user interface to communicate, for example display, the first and second usage information. In this way, the subject is informed of their usage of the first and second medicaments respectively. In the case of the first or second medicament being, for instance, a rescue medicament, the system may enable the subject to track the status of their respiratory disease. In the case of the first or second medicament being, for example, a maintenance medicament, the system may enable the subject to track their adherence to, or compliance with, a predetermined treatment regimen. In some examples, the processing module is configured to control the user interface to display the first and second usage information simultaneously, such as in a single graphical user interface (GUI).

Further, in some examples, the system further comprises at least one third inhaler. One or more (or each) of the at least one third inhaler is configured to deliver a third medicament to the subject. This may be, for example, the same subject to whom the first and second medicaments are administered via the first inhaler and the second inhaler respectively. The third medicament is different from the first and second medicaments. One or more (or each) of the at least one third inhaler may, for example, comprise a third medicament reservoir containing the third medicament.

One or more (or each) of the at least one third inhaler comprises a third use determination system configured to determine a third value of a usage parameter relating to use of the respective third inhaler. The usage parameter may, for instance, comprise a use of, such as an inhalation of the third medicament performed by the subject using, the respective third inhaler. Alternatively or additionally, the usage parameter may comprise a parameter relating to airflow during inhalation of the third medicament performed by the subject.

In a non-limiting example, the first medicament is a rescue medicament for use by the subject as needed, the second medicament is a maintenance medicament which is used by the subject according to a predetermined treatment regimen, and the third medicament is a further maintenance medicament which is used by the subject according to a further predetermined treatment regimen.

In a non-limiting example, the first medicament is albuterol (sulfate), and the second medicament is salmeterol (xinafoate) combined with fluticasone (propionate or furoate), budesonide combined with formoterol (fumarate), or beclomethasone (dipropionate).

In some non-limiting examples, the system comprises two or more first inhalers, such as two, three, four, five, or more first inhalers. Such a plurality of first inhalers may be particularly advantageous when, for example, the first medicament is a rescue medicament. In such an example, the subject may place first inhalers in various different locations, such as on a nightstand, in a gym bag, in a vehicle, and so on, in order that the rescue medicament is readily available if needed.

In other non-limiting examples, the first medicament is a maintenance medicament. In such an example, the subject may place first inhalers in various different locations in order to facilitate administration of the maintenance medicament at points during the subject's daily routine, thereby assisting the subject to adhere to the treatment regimen associated with the maintenance medicament.

Further, in some examples, the processing module may include a computer program that resides, for example, on the user device. The computer program comprises computer program code which is adapted, when the computer program is run on a computer, such as the user device, to implement the methods and technique described herein. The embodiments described herein for the system are applicable to the method and the computer program. Moreover, the embodiments described for the method and computer program are applicable to the system.

The system may also include a processing module, which may be referred to as a digital health platform (DHP), that receives and aggregates inhaler data (e.g., usage events) from inhalers that are associated with a plurality of different users. In some examples, the DHP may reside on one or more servers, and may include computer software configured to perform the functions described in relation to the DHP. For example, the DHP may include a dashboard application that may be accessible by a computer or server associated with a health care provider, such as a hospital or hospital system, a health system, a medical group, a physician, a clinic, and/or a pharmaceutical company. In some examples, the dashboard application is a web application (e.g., a web portal). For example, the DHP is also configured to provide data, such as inhaler data, to clinicians and physicians through the use of the dashboard application (e.g., via a REST API).

The DHP is configured to receive and store inhaler data from processing modules residing on user devices (e.g., the patient-facing mobile applications), and is configured to provide data to a computer or server associated with a health care provider (e.g., via the dashboard application). The inhaler data may include any of the data described with reference to the inhalers described herein, such as usage events, error events, inhalation profiles, associated timestamps, medicament types, etc. The inhaler data may be associated with an inhaler and/or a user profile, for example, at the processing module (e.g., residing on the user device) and/or at the DHP. The DHP may also de-identify (e.g., unassociate) the inhaler data from a particular user, and the DHP may perform analytics on de-identified data relating to the inhalers, such that the DHP (e.g., or a user of the DHP) is unaware of the particular user that the inhaler data is associated with.

However, in many examples, the DHP does not have a direct connection with the inhaler, and as such, the DHP is unable to verify (directly verify with the inhaler) the completeness of the usage data it has received. Further, in some examples, the DHP cannot communicate to the inhaler, and the inhaler cannot communicate directly to the DHP. This creates a technical problem as to how the DHP can perform data verification without a line of communication with the inhaler that is capturing usage events. That is, as the DHP is not in direct communication with the inhaler that is capturing the usage events, the DHP is unable to perform data verification of the usage events.

The DHP may be configured to enable, and in some instances initiate, the transfer of data (e.g., inhaler data) from the processing modules (e.g., the processing modules residing on user devices). For example, the DHP may expose a representational state transfer (REST) application programming interface (API), which may be used to access or update the data maintained by the DHP. In response, the processing modules residing on the user devices may access the data through the REST API. In some examples, the processing module on the user device may be configured to periodically send, such as every 15 minutes, inhalation data (e.g., or an indication that there is no new inhalation data) to the DHP, for example, via the REST API exposed by the DHP. The DHP may receive the patient's consent to access the patient's data via their respective processing module residing on their user device. In addition, the DHP may also store incoming data from dedicated mobile and web applications. Again, the DHP may receive the patient's consent, incoming data, etc., through the REST API.

The DHP may cause the computer or server associated with (e.g., operated by) the health care provider to provide inhaler data to practitioners and health care professionals to allow them to view inhaler data specific to a program to which a patient has consented. In one example, the DHP causes the computer or server associated with the health care provider to provide the inhalation data via a GUI that is presented on a display device associated with the health care provider's computer.

The DHP may define any number of programs, which in some instances may be configured and altered by a health care provider. When providing inhaler data to a health care provider, the DHP may provide a GUI (e.g., may be configured to display a GUI) that is specific to a particular program associated with that health care provider. A program defines a set of criteria, such as types of medications (e.g., any combination of rescue and/or maintenance medications), specific patients and in turn their applicable inhalers, other users of the programs such as particular physicians, practice groups, and/or administrators, the types of data presented to the health care provider such as charts, event tables, usage summaries, etc. The health care provider may configure and establish any number of programs using the DHP. Further, a particular patient and their inhalers may be associated with any number of unique programs. In some examples, the programs are stored and maintained by the DHP, and the computer associated with the health care provider is configured to access the data relevant to each program from the DHP using, for example, an application, such as a dashboard or web application. In such examples, and once a program is established, the DHP is configured to receive inhaler data associated with the program, analyze and manipulate the inhaler data to the extent necessary, and provide program data (e.g., via the dashboard) to the health care provider. The program data may include inhaler data that is specific to the configuration of a particular program, and for example, additional data that is derived from the inhaler data, as is described in more detail below. For example, the DHP may enable a GUI, such as those described herein, on the computer associated with the health care provider that presents the program data to the health care provider.

Further, although described primarily with respect to inhaler data, it should be appreciated that the system described herein may aggregate data from any combination of therapeutic devices or areas. In such examples, the DHP may configure programs that also define particular therapeutic devices or areas, such as those described herein. That is, the DHP is configured to maintain and analyze data for a plurality of disease types, medical devices, and/or medications.

Health care providers have a limited amount of time and resources to analyze data associated with their patient's use of their medical devices. And further, different usage characteristics, such as underuse, overuse, and various types of improper use of a medical device, may have varying degrees of relevance or importance to a physician based on the type of medical device and/or the medicament type provided by the medical device. For example, for some medicament types, an indication of overuse is more concerning than an indication over underuse, or vice versa. For instance, overuse of a rescue medicament inhaler suggests that the user is experiencing a high number of exacerbations and has poor control of their respiratory condition. And an underuse of a maintenance inhaler indicates that the user is not adhering to their prescribed dosing schedule, which suggests that the user has not been properly informed as to their dosing regimen, that the user is overprescribed and does not need that particular dose concentration or regimen and is cutting back intentionally, and/or that the user is not taking their respiratory condition seriously.

Moreover, some health care providers have a significantly large number of patients who may each use a variety of inhalers, each comprising the same or different medication types. For these health care providers, the data provided by a digital inhaler system can be overwhelmingly large and cumbersome to efficiently review to properly diagnose high risk patients and/or patients with poor adherence or compliance with their treatment regimen. For instance, some health care providers may have hundreds of patients who use a digital inhaler system, and each of these patients may have multiple inhalers, where these multiple inhalers may include the same or different medication types.

Accordingly, the DHP may analyze and manipulate the digital data received from a vast number of digital inhaler systems to generate a subset or filtered list of users and/or inhalers that, for example, present a health care provider with those users and/or medication types that are indicative of patients who are high risk and/or poor adherence or compliance with their treatment regimen. For instance, the DHP may be configured to generate a filtered list of users based on the plurality of usage events and one or more variables. For example, the DHP may determine a medication type(s), a time of day, and/or a date range. For example, the DHP may receive a selection (e.g., from a user) of a medication type(s), a time of day, and/or a date range. The DHP may determine the medication type, the type of day, and/or the date range using computer logic. For example, the DHP may receive a user selection for one or more of the medication type, the time of day, and/or the date range, and the DHP may be configured to automatically determine the remainder of the medication type, the time of day, and/or the date range using computer logic (e.g., based on previously selected options or analytics based on the particular users and/or usage events of the program). The medication type(s) may include one or more rescue medication types and/or one or more maintenance medication types. The time of day may include, for example, daytime (e.g., defined as between 8 am and 8 pm), nighttime (e.g., defined as between 8 pm and 8 am), and all day. Alternatively or additionally, time of day may include a customizable definition of a time period, such as between a start time (e.g., 10 pm) and an end time (e.g., 6 am). The date range may include a start and end date, or may include a selection of a preconfigured, dynamically adjusted date range, such as the last week(s), last month, etc.

The DHP may determine a subset of the usage events based on the determined medication type, the determined time of day, and/or the determined date range. For example, the DHP may apply a usage event filter to filter the plurality of usage events received from a plurality of different inhalers to determine a subset of usage events based on the determined medication type, the determined time of day, and/or the determined date range.

The DHP may determine an inhalation count threshold. For example, the DHP may receive a selection of the inhalation count threshold, for instance, from a user. The inhalation count threshold may be a number. The DHP may determine a number of usage events out of the subset of usage events that are associated with the same user and medication type. For example, the DHP may associate (e.g., group or combine) usage events out of the subset of usage events that have a common user and medication type. The DHP may determine a filtered list of users out of the plurality of users based on a comparison of the selected inhalation count threshold with the number of usage events that are associated with the same user and medication type. For example, the DHP may apply an inhalation count threshold filter to generate the filtered list of users. For instance, the DHP may compare the combined usage events that have the common user and medication type to the inhalation count threshold and a criteria (e.g., less than, greater than, less than or equal to, greater than or equal to, etc.). If the combined usage events do meet the inhalation count threshold and criteria (e.g., are great than, or, alternatively are less than the inhalation count threshold), the DHP may include the user associated with the combined usage events in the filtered list of users. However, if the combined usage events do not meet the inhalation count threshold and the criteria, the DHP may ignore (e.g., discard) the user associated with the combined usage events. The DHP may generate a graphical user interface (GUI) (e.g., via a display device of a remote computer terminal) that comprises the number of usage events for each user of the filtered list of users.

Further, in some examples, the DHP may be configured to store a filter based on the determined medication type, the determined time of day, the determined date range, the selected inhalation count threshold, and/or the criteria. The DHP may associate the filter with the program so that the filter may be selected by a plurality of different heath care providers who are associated with an organization and the program. Further, in some examples, the DHP may be configured to apply the filter to other programs associated with the organization and/or outside of the organization.

In addition to or as an alternative to comparing the subset of usage events to an inhalation count threshold, the DHP may be configured to compare different subsets of usage events to one another, where for instance, the different subsets of usage events may be associated with the same users. For example, the DHP may determine whether the number (e.g., the total number) of usage events that are associated with the same user and medication type of a first subset of usage events is proportionally smaller than or proportionally greater than the number (e.g., the total number) of a different, non-overlapping subset of the usage events that are associated with the same user and medication type. In some instances, the different, non-overlapping subset of usage events is associated with a different date range than the number of usage events, but is associated with the same medication type and time of day. For example, the DHP may be configured to determine the users out of the subset of users who had more than X % increase (e.g., 50% increase) in usage events over a period of time (e.g., this week) for a particular medication type (e.g., a rescue medication type) as compared to a different time period (e.g., the previous week). As another example, the DHP may be configured to determine the users out of the subset of users who had more than an X % decrease (e.g., 50% decrease) in usage events over a period of time (e.g., this week) for a particular medication type (e.g., a maintenance medication type) as compared to a different time period (e.g., the previous week). This analysis will, for example, help health care providers quickly and easily identify those users who are at risk and/or exhibiting a decrease in the adherence or compliance to their treatment regimen.

As noted, some health care providers have a significantly large number of patients who may each use a variety of inhalers, each comprising the same or different medication types. The DHP, through the use of the analytics and analysis described herein, may be configured to reduce the resulting patient lists provided to the provider in the upwards of 50% or 60%, or more preferably 70%-80%, or most preferably 90+%. That is, a filtered list of users generated by the DHP might include only 40% or 50% of the plurality of users, or more preferably might include only 20%-30% of the plurality of users, or most preferably might include less than or equal to 10% of the plurality of users. In some examples, one or more thresholds (e.g., such as an inhalation count threshold) may be selected such that this degree of filtering is achieved. This enables a provider to quickly and effectively diagnose those patients who are at the most risk of an exacerbation and/or are experiencing the most significant reduction in their adherence or compliance to their treatment regimen. This can assist the provider in the ongoing task of improving the clinical outcomes for the plurality of users. It balances the power of the available analytics and analysis with the need for the provider to take ultimate responsibility for the treatment of each patient.

In some examples, each usage event further comprises inhalation data, and the DHP may be configured to determine a percentage of good inhalations for the number of usage events for each user of the filtered list. The percentage of good inhalations may include an indication of a percentage usage events (e.g., out of the number of usage events that are associated with the same user and medication type) where the associated inhalation data is above a threshold. A GUI generated by the DHP may further comprise an indication of the percentage of good inhalations for the number of usage events for each user of the filtered list. The inhalation data may include a peak inspiratory flow (PIF), total inhaled volume, inhalation time, a time to peak inhalation flow, etc. of the usage event.

The DHP may determine a last synchronization time for each of the plurality of inhalers. The last synchronization time may indicate the most recent time the inhaler was connected with an application residing on a user device. The DHP may also determine an all-connected duration that indicates the last time that all of the inhalers of a particular medication type associated with a user have a confirmed connection between the inhaler and the application residing on the user device associated with the user, regardless of whether a usage event was transferred during the connection between the inhaler and the user device. The all-connected duration may indicate a number of hours or a number of days. The all-connected duration may indicate the oldest last synchronization time of the inhalers of the particular medication type associated with the user. The all-connected duration may assist the physician in determining whether the user may have inhalers where usage events were recorded, but never transferred to the DHP.

The DHP may generate a GUI with a listing of users that prioritizes users with an inhaler that has zero usage events and a confirmed connection between the inhaler and the application residing on the user device within a time frame over users with an inhaler that has zero usage events without a confirmed connection between the inhaler and the application residing on the user device within the time frame, for example, as described in more detail herein.

The usage events collected from the variety of inhalers may include inhalation data. One measure of the inhalation data may be most the most indicative measure of whether the usage event included an inhalation by the user (e.g., as opposed to other, non-user based factors that might trigger a false-positive inhalation measure). However, a different, other measure of the inhalation data may provide insights to the physician on the efficacy of the user's inhalation. Since the DHP receives a plurality of usage events associated with a plurality of different inhalers and users over varying time periods, this create a technical challenge of how to generate the appropriate data indicating the efficacy of the user's inhalations without the inclusion of false-positive events.

The DHP may receive a plurality of usage events, where each usage event includes inhalation data from an inhaler of a particular medication for a user. The DHP may determine to a subset of the usage events based on a comparison of a first inhalation metric of the usage events to one or more thresholds. The DHP may determine the subset of usage events by removing (e.g., filtering out) the usage events that do not reside between a lower threshold and an upper threshold. The DHP may categorize the subset of usage events based on a second inhalation metric that is different from the first inhalation metric. The first and second inhalation metrics may include PIF, total inhaled volume, inhalation duration, a time to peak inhalation flow, etc. For example, the DHP may categorize the subset of usage events between an upper value and a lower value based on the second inhalation metric (e.g., between 0.3 L and 6 L in the example of inhalation volume). In some instances, the DHP may generate a GUI (e.g., via a display device of a remote computer terminal) that comprises the subset of usage events and the associated second inhalation metric for each of the subset of usage events relative to the upper and lower values. The GUI may include a scatter chart of the subset of usage events and the associated second inhalation metric for each. The GUI may include a trend line across the subset of usage events, where for instance, the DHP may determine the trend line using a LOESS (Locally Estimated Scatterplot Smoothing) algorithm with a smoothing factor (e.g., a smoothing factor of 0.5).

In some example, the DHP may determine the subset of the usage events by comparing the first inhalation metric to a lower threshold and an upper threshold, wherein the subset of usage events are those usage events where the first inhalation metric is between the lower threshold and the upper threshold. The first inhalation metric may, for example, be a peak inhalation flow (PIF) of the usage event, and the second inhalation metric may be the inhalation volume of the usage event. For instance, if the second inhalation metric comprises inhalation volume, then the DHP may categorize the subset of inhalation metrics between an upper value associated with the second inhalation metric (e.g., 6 L) and a lower value associated with the second inhalation metric (0.3 L).

The DHP is configured to manipulate data differently and/or generate different alerts based on the specific medications, patients, users (e.g., health care provides), and/or therapeutic devices or areas defined by the program. As one example, the DHP may be configured to generate a first type of alert when a rescue medicament type and one or more maintenance medicament types are included in the program, but generate a second type of alert when the rescue medicament type is not included in the program. For instance, the DHP may be configured to generate a first alert that indicates a prioritized listing of users with the highest number of usage events (e.g., over a particular time range, such as one week) of inhalers that include a rescue medicament type when the rescue medicament type and one or more maintenance medicament types are included in the program, and generate a second alert that indicates a prioritized listing of users with the lowest number of usage events (e.g., over a particular time range, such as one month) of inhalers that include the maintenance medicament type when the rescue medicament type is not included in the program. In some examples, the alert is provided via a display device that, for example, may reside at a health care provider facility.

For example, the DHP may be configured to prioritize data, such as patient lists, differently based on the specific medication types, patients, users (e.g., health care providers), and/or therapeutic devices or areas defined by the program. In some examples, the DHP is configured to prioritize data indicating high usage of a rescue inhaler over data indicating a low usage of a rescue inhaler and over data indicating either a high or low usage of a maintenance inhaler. For example, if a program includes rescue medicaments and one or more maintenance medicaments for a group of users associated with the program, the DHP may be configured to prioritize the users with the highest number of usage events of their inhaler(s) that include the rescue medicament over the users with a lower number of usage events of their inhaler(s) that include the rescue medicament and over the users with the highest or lowest number of usage events of their inhaler(s) with a maintenance medicament. However, if rescue inhalers are not part of the program, then the DHP is configured to prioritize users with the lowest number of usage events of their inhalers(s) that include a particular maintenance medicament, over users with the highest number of usage events of their inhaler(s) that include the particular maintenance medicament. Further, in some instances, the DHP may prioritize users with the highest usage events of their inhaler(s) that include the rescue medicament only when there is at least one user in the program who has a number of usage events for their rescue inhaler(s) that exceeds a threshold amount in a period of time, such as 5 usage events within the past week, and otherwise, may prioritize the users with the lowest number of usage events of their inhalers(s) that include a particular maintenance medicament.

The DHP may be configured to determine an all-connected duration for each medicament type associated with each user. For example, the DHP may be configured to determine a group of inhalers that are all associated with one user and that all include the same medicament. The DHP may be configured to then determine the last synchronization time for all of those inhalers. Next, the DHP may be configured to determine the oldest or least recent last synchronization time from the group and set this time as the all-connected duration for that particular medicament type for that particular user. The DHP may be configured to generate an alert that indicates the all-connected duration, the medicament type, and the user. In some examples, the alert is provided via a display device that, for example, may reside at a health care provider facility.

For example, in a non-limiting example, the DHP is configured to prioritize users based on the all-connected time for a particular medicament type. For instance, the DHP may generate an alert (e.g., a GUI) that prioritizes users with the oldest all-connected time for their inhaler(s) of a particular maintenance medicament type, when that maintenance medicament is part of the program, but otherwise, prioritize users in another manner, such as based on the users with the highest number of usage events of their inhaler(s) that include the rescue medicament or based on the users with the lowest percentage of good inhalations (e.g., while excluding all users with 0% good inhalations), possible of a particular medicament type. As such, the DHP may be configured to prioritize data, such as patient lists, differently based on the specific medication types that are included in the program.

As noted above, the DHP is configured to receive and aggregate inhaler data from inhalers that are associated with a plurality of different users. However, particularly in situations where the inhaler is configured to first communicate with a user device prior to the DHP receiving the inhaler data, the DHP may not have a complete history of usage events for each inhaler that is part of a program. For example, there may be some inhalers that have recorded usage events but have not connected to an associated user device, and as such, have not transferred their usage events to the user device or to the DHP. But, the DHP may calculate zero usage events for two different inhalers, when in fact, one of those inhalers may have recorded usage events but has not transferred those usage events to the DHP, while the other inhaler has in-fact not been used. That is, the DHP may include data from many inhalers that have zero dosage events over a particular period of time, such as the past week or month. However, some of these inhalers may not have actually been used by their user, while other inhalers may or may not have been used, but the DHP may be unaware of the reliability of the usage data. This can distort the data presented by the DHP and cause confusion for health care providers who are reviewing the data relating to one of their programs. For example, listing inhalers (or users associated with inhalers) based on the least number of usage events will create a distorted view of inhalers by comingling inhalers that have not had any usage events with inhalers that have had one or more usage events, but the data associated with these events has not yet been received by the DHP. Therefore, sorting on a descending basis of the number of usage events will result in a list of inhalers that does not provide an accurate indication of those users who are not adherent with their dosing regimen.

As such, the DHP is configured to determine and differentiate users who are associated with inhalers that have a true zero number of usage events from users who are associated with inhalers that appear to have zero usage events from the DHP's perspective but have not connected to their associated user device (or directly to the DHP) within a particular time period. For example, the DHP is configured to determine a last synchronization time for each of the plurality of inhalers. The last synchronization time indicates the last time the inhaler was connected with a user device that includes a mobile application (e.g., or, alternatively, connected directly to the DHP), regardless of whether usage events were transferred as part of the connection. Further, it should be appreciated that some inhalers may be configured to be connected to multiple different user devices (e.g., such as a user's smartphone and their tablet), and as such, the last synchronization time indicates the last the inhaler was connected with any user device that includes a mobile application.

The DHP may calculate the last synchronization time using the time stamps that are associated with usage events. For example, when the inhaler connects with the processing module residing on the user device, the processing module may indicate a time denoting the last time the inhaler connected to a mobile application or a time of the most recent usage event acquired from the inhaler. In response, the inhaler may send only those usage events that postdate that time. The processing module may later send these usage events and an indication of the time of the connection between the inhaler and the processing module to the DHP. For example, the processing module on the user device may be configured to send inhalation data (or an indication that there is no new inhalation data) to the DHP periodically, such as every 15 minutes. As such, the DHP may determine a last synchronization time for each inhaler that indicates the last time the inhaler was connected with a user device that includes a mobile application (e.g., or, alternatively, connected directly to the DHP), for example, regardless of whether usage events were transferred as part of the connection.

The DHP may be configured to generate an alert that indicates the users that are associated with an inhaler with zero doses and a confirmed connection within a time frame. In some examples, the DHP may cause a display device (e.g., associated with a health care provider) to present an alert (e.g., a GUI) that includes a listing of users, where the listing prioritizes users with an inhaler that has zero usage events and a confirmed connection between the inhaler and the application residing on the user device within a time frame over users with an inhaler that has zero usage events without a confirmed connection between the inhaler and the application residing on the user device within the time frame. In some examples, the inhalers all include a maintenance medicament type. For example, the program may be limited to inhalers that include a maintenance medicament type. Further, in some examples, the time frame may be the last month or the last 30 days.

As noted above, some users will have multiple inhalers that include the same medicament. For example, a user may have multiple inhalers that include a rescue medicament (e.g., and keep them at different locations). Further, a user may have multiple inhalers that include a particular maintenance medicament, such as when they are transitioning between refills. As such, the DHP may be unaware of how complete and trustworthy the data is for each patient in instances where a patient has multiple inhalers that include the same medicament, because for example, there still may be instances where an inhaler has not connected with the user device for a period of days, weeks, or even months. Also as noted above, the DHP is configured to determine a last synchronization time for each of the plurality of inhalers. Further, the DHP may also be configured to determine whether the user has multiple assigned inhalers that include the same medicament (e.g., such as a rescue medicament), and then determine the oldest, or least recent, last synchronization time of the inhalers of a particular medication type that are associated with the user. This may be referred to as an all-connected duration, which represents the oldest, or least recent, last synchronization time of all the inhalers of a particular medication type that are associated with the user. For example, if a user is associated with two inhalers that include a rescue medicament, such as inhaler 1 and inhaler 2, and inhaler 1 has a last synchronization time of 2 days ago, but inhaler 2 has a last synchronization time of 10 days ago, the user will be associated with an all-connected duration for their rescue medicament inhalers of 10 days ago.

The DHP may be configured to generate an alert (e.g., a GUI) that indicates a listing of a plurality of users and the all-connected duration for each medicament type associated with each user. As noted above, the all-connected duration may indicate the last time that all of the inhalers of a particular medication type associated with the user have a confirmed connection between the inhaler and the application residing on the user device associated with the user, for example, regardless of whether a usage event was transferred during the connection. In some examples, the all-connected duration indicates a number of hours, days, weeks, or even months.

The system may include devices and users that are located in various different time zones, which may fluctuate from day-to-day. As such, the data captured by the system may also be associated with various time zones. However, the inhalers may be unaware of their time zone (e.g., they may only include short range personal area network communication capability), and the health care provider may be unaware of the time zone of usage events for each user. Nonetheless, the DHP is challenged when determining a cohesive manner to provide an alert or feedback to a health care provider when the data is associated with a variety of different time zones, medicament types, and usage events.

As noted above, in some examples, the use determination system of an inhaler may start an internal counter (e.g., which counts up from 0 indefinitely) when, for example, the use determination system is woken out of an energy-saving sleep mode for the first time (e.g., after the mouthpiece cover is opened for the first time). Thereafter, any time-and-date stamp generated by the use determination system may be a relative time (or count) based on the internal counter of the clock module. And, when the inhaler connects with the processing module residing on the user device, the processing module may indicate a time denoting the last time the inhaler connected to a mobile application or a time of the most recent usage event acquired from the inhaler. In response, the inhaler may send only those usage events that postdate that time. The processing module may receive one or more usage events and associated timestamps (e.g., a relative count from the internal counter) from the inhaler. The processing module may determine a local mean time and a time zone for a timestamp, and associated the local mean time and time zone with the usage event. The time zone may be that of the processing module at the time of receiving the usage event, or may be the time zone of the processing module at the time associated with the usage event. The processing module may then send the usage event and the associated local mean time and time zone to the DHP. The DHP may associate the usage event, local mean time, and time zone with a user.

Next, when accessed by a health care professional, the DHP may generate alerts that are specific to the users, inhalers, and/or medicaments of the program selected by the health care professional based on the time zones of the most recent usage event associated with the user. For example, the DHP may determine a time frame (e.g., time window) based on the medicament type and the most recent usage event. And the DHP may generate an alert (e.g., GUI) that indicates all the user's usage events within the time window. The DHP may determine the time window based on the most recent usage event, based on the time zone of the usage event, plus an addition N days (e.g., where N=6 for rescue medicament, and N=29 or 30 for maintenance medicament). For instance, if the medicament type is a rescue medicament type, and the user's most recent usage event occurred at 8:30 am Jun. 30, 2020 (GMT+9), then the time window will include Jun. 30, 2020 and the previous 6 days. However, if the medicament type is a rescue medicament type, and the user's most recent usage event occurred at 7:30 pm on Jun. 29, 2020 (GMT−5), then the time window will include Jun. 29, 2020 and the previous 6 days. Therefore, although the usage event occurred at the same time, the time window for each alert is selected differently based on the local time zone of the most recent usage event for that user (e.g., regardless of the time zone of the health care provider).

Further, when accessed by a health care professional, the DHP may determine a time zone of the health care professional, and the DHP may generate alerts that are specific to the users, inhalers, and/or medicaments of the program selected by the health care professional based on the time zone of the health care professional (e.g., in addition to, or in lieu of the alerts that are based on the time zones of the most recent usage event associated with the user). For example, the DHP may generate alerts that indicate a plurality of usage events, the user associated with each usage event, and the associated local mean time of the usage event. Then, only for the usage events that are associated with a time zone that is different from the time zone of the health care professional, the DHP may also generate alerts that indicate the time zone of the usage event. So, in some examples, the DHP may determine a time frame (e.g., time window) based on the medicament type and the most recent usage event for a user, and then generate an alert (e.g., GUI) that indicates all the user's usage events within the time window for that user, while also including the time zone for each usage event only where it differs from the time zone associated with the health care provider.

These features, and others, will be described in more detail below with respect to the following Figures.

FIG. 1 shows a block diagram of an inhaler 100 according to an example. The inhaler 100 comprises a use determination system 12 which determines at least one value of a usage parameter. The usage parameter may be referred to as a usage event. The at least one value of the usage parameter is received by a transmission module 14, as represented in FIG. 1 by the arrow between the block representing the use determination system 12 and the block representing the transmission module 14. The transmission module 14 encrypts data based on the value(s) of the usage parameter, and transmits the encrypted data, as represented in FIG. 1 by the arrow pointing away from the transmission module 14 block. The transmission of the encrypted data by the transmission module 14 may, for example, be wireless, as previously described.

The usage parameter may, for example, comprise a use of the respective inhaler. In a relatively simple implementation, the at least one value may comprise "TRUE" when use of, for example an inhalation using, the respective inhaler has been determined, or "FALSE" when no such use of the respective inhaler is determined.

The use determination system 12 may include one or more components used to determine at least one value of a usage parameter of inhaler 100. The usage parameter may be one or more of a count of the number of uses inhaler 100, a measure of airflow of inhaler 100, and/or other measurements indicating the usage of the medicament of inhaler 100. The use determination system 12 may include one or more of a switch configured to detect usage of inhaler 100, one or more sensors configured to detect use of inhaler 100, one or more buttons configured to be depressed upon use of inhaler 100, and/or the like.

For example, the use determination system 12 may, for instance, comprise a mechanical switch configured to be actuated prior to, during, or after use of the respective inhaler. The mechanical switch may indicate that a dose of medicament has been primed and is ready for inhalation (e.g., such as by metering a dose from a hopper, advancing and/or opening a blister pack, etc.). In a non-limiting example, the inhaler 100 comprises a medicament reservoir (not visible in FIG. 1), and a dose metering assembly (not visible in FIG. 1) configured to meter a dose of the rescue medicament from the reservoir. The use determination system 12 may be configured to register the metering of the dose by the dose metering assembly, each metering being thereby indicative of the inhalation performed by the subject using the inhaler 100. Accordingly, the inhaler 100 may be configured to monitor the number of inhalations of the medicament, since the dose should be metered via the dose metering assembly before being inhaled by the subject. One non-limiting example of the dose metering assembly will be explained in greater detail with reference to FIGS. 12-16.

Alternatively or additionally, the use determination system 12 may register each inhalation in different manners and/or based on additional or alternative feedback. For example, the use determination system 12 may be configured to register an inhalation by the subject when the feedback from a suitable sensor (not visible in FIG. 1) indicates that an inhalation by the subject has occurred, for example when a pressure measurement or flow rate exceeds a predefined threshold associated with a successful inhalation.

A sensor, such as a pressure sensor or acoustic sensor, may, for example, be included in the use determination system 12 in order to register each inhalation. Such a sensor may be an alternative or in addition to the abovementioned mechanical switch. When a pressure or acoustic sensor is included in the use determination system 12, the pressure sensor may, for instance, be used to confirm that, or assess the degree to which, a dose metered via the dose metering assembly is inhaled by the subject, as will be described in greater detail with reference to FIGS. 2 and 12-16.

More generally, the use determination system 12 may comprise a sensor for detecting a parameter relating to airflow during inhalation of the respective medicament performed by the subject. In other words, the usage parameter comprises a parameter relating to airflow during inhalation of the medicament. The at least one value may thus, for example, comprise a numerical value relating to the detected inhalation parameter.

The inhalation parameter may be, for example, at least one of a peak inhalation flow (PIF), an inhalation volume, a time to peak inhalation flow, and/or an inhalation duration. In such examples, the at least one value comprises a numerical value for the peak inhalation flow, the inhalation volume, the time to peak inhalation flow, and/or the inhalation duration.

A pressure sensor may be particularly suitable for measuring the parameter, since the airflow during inhalation by the subject may be monitored by measuring the associated pressure changes. As will be explained in greater detail with reference to FIGS. 12-16, the pressure sensor may be located within or placed in fluid communication with a flow pathway through which air and the medicament is drawn by the subject during inhalation. Alternative ways of measuring the parameter, such as via a suitable flow sensor, can also be used.

An inhalation may be associated with a decrease in the pressure in the airflow channel of the inhaler relative to when no inhalation is taking place. The point at which the pressure change is at its greatest may correspond to the peak inhalation flow. The pressure sensor may detect this point in the inhalation.

The pressure change associated with an inhalation may alternatively or additionally be used to determine an inhalation volume. This may be achieved by, for example, using the pressure change during the inhalation measured by the pressure sensor to first determine the flow rate over the time of the inhalation, from which the total inhaled volume may be derived.

The pressure change associated with an inhalation may alternatively or additionally be used to determine an inhalation duration. The time may be recorded, for example, from the first decrease in pressure measured by the pressure sensor, coinciding with the start of the inhalation, to the pressure returning to a pressure corresponding to no inhalation taking place.

The inhalation parameter may alternatively or additionally include the time to peak inhalation flow. This time to peak inhalation flow parameter may be recorded, for example, from the first decrease in pressure measured by the pressure sensor, coinciding with the start of the inhalation, to the pressure reaching a minimum value corresponding to peak flow.

Figure 2:
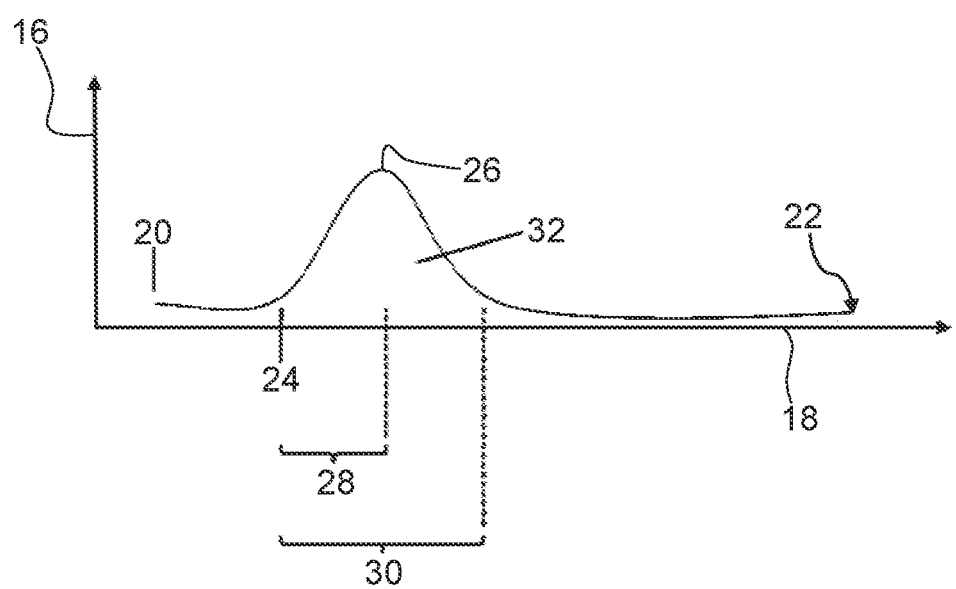
FIG. 2 is a graph of example flow rate versus time during use of an inhaler.

FIG. 2 shows a graph of flow rate 16 versus time 18 during use of an inhaler 100 according to a non-limiting example. The use determination system 12 in this example comprises a mechanically operated switch in the form of a switch which is actuated when a mouthpiece cover of the inhaler 100 is opened. The mouthpiece cover is opened at point 20 on the graph. In this example, the use determination system 12 further comprises a pressure sensor.

When the mouthpiece cover is opened, the use determination system 12 is woken out of an energy saving sleep mode, and a new inhalation event is registered. The inhalation event is also assigned an open time corresponding to how much time, for example milliseconds, elapses since the inhaler 100 wakes from the sleep mode. Point 22 corresponds to the cap closing or 60 seconds having elapsed since point 20. At point 22, detection ceases.

Once the mouthpiece cover is open, the use determination system 12 looks for a change in the air pressure, as detected using the pressure sensor. The start of the air pressure change is registered as the inhale event time 24. The point at which the air pressure change is greatest corresponds to the peak inhalation flow 26. The use determination system 12 records the peak inhalation flow 26 as a flow of air, measured in units of 100 mL per minute, which flow of air is transformed from the air pressure change. Thus, in this example, the at least one value comprises a value of the peak inhalation flow in units of 100 mL per minute. The corresponding usage information provided via the user interface may, for example, express this peak inhalation flow using the same units or in liters per minute.

The time to peak inhalation flow 28 corresponds to the time taken in milliseconds for the peak inhalation flow 26 to be reached. The inhalation duration 30 corresponds to the duration of the entire inhalation in milliseconds. The area under the graph 32 corresponds to the inhalation volume in milliliters.

The usage information provided via the user interface may, additionally or alternatively to providing the inhalation parameter(s) as numerical values, provide a classification of one or more (or each) inhalation event(s). For example, if the peak inhalation flow is between 0 and 30 liters per minute, the inhalation event is classified as "low inhalation" (less than or equal to 30 liters per minute) or as "no inhalation", if no inhalation is detected within 60 seconds of the mouthpiece cover being open. If the peak inhalation flow is greater than 45 and less than or equal to 200 liters per minute, the inhalation event is classified as a "good inhalation". If the peak inhalation flow is greater than 30 and less than or equal to 45 liters per minute, the inhalation event is classified as "fair". If the peak inhalation flow is above 200 liters per minute, the inhalation event is classified as a "possible air vent block". The inhalation event may be classified as an "exhalation", which may be sensed by airflow being detected in the opposite direction to that expected for inhalation using the inhaler 100.

In a non-limiting example, the inhaler is configured such that, for a normal inhalation, the medicament is dispensed approximately 0.5 seconds following the start of the inhalation. A subject's inhalation only reaching peak inhalation flow after the 0.5 seconds have elapsed, such as after approximately 1.5 seconds, may be partially indicative of the subject having difficulty in controlling their respiratory disease. Such a time to reach peak inhalation flow may, for example, be indicative of the subject facing an impending exacerbation.

More generally, the use determination system 12 may employ respective sensors (e.g. respective pressure sensors) for registering an inhalation/use of the inhaler and detecting the inhalation parameter, or a common sensor (e.g. a common pressure sensor) which is configured to fulfil both inhalation/use registering and inhalation parameter detecting functions.

Any suitable sensor may be included in the use determination system 12, such as one or more pressure sensors, temperature sensors, humidity sensors, orientation sensors, acoustic sensors, and/or optical sensors. The pressure sensor(s) may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology.

In a non-limiting example, the use determination system 12 comprises a differential pressure sensor. The differential pressure sensor may, for instance, comprise a dual port type sensor for measuring a pressure difference across a section of the air passage through which the subject inhales. A single port gauge type sensor may alternatively be used. The latter operates by measuring the difference in pressure in the air passage during inhalation and when there is no flow. The difference in the readings corresponds to the pressure drop associated with inhalation.

In another non-limiting example, the use determination system 12 includes an acoustic sensor. The acoustic sensor in this example is configured to sense a noise generated when the subject inhales through the respective inhaler 100. The acoustic sensor may include, for example, a microphone. The respective inhaler 100 may, for instance, comprise a capsule which is arranged to spin when the subject inhales though the device; the spinning of the capsule generating the noise for detection by the acoustic sensor. The spinning of the capsule may thus provide a suitably interpretable noise, e.g. rattle, for deriving use and/or inhalation parameter data.

An algorithm may, for example, be used to interpret the acoustic data in order to determine use data and/or the parameter relating to airflow during the inhalation. For instance, an algorithm as described by P. Colthorpe et al., "Adding Electronics to the Breezhaler: Satisfying the Needs of Patients and Regulators", Respiratory Drug Delivery 2018, 1, 71-80 may be used. Once the generated sound is detected, the algorithm may process the raw acoustic data to generate the use and/or inhalation parameter data.

Figure 3:
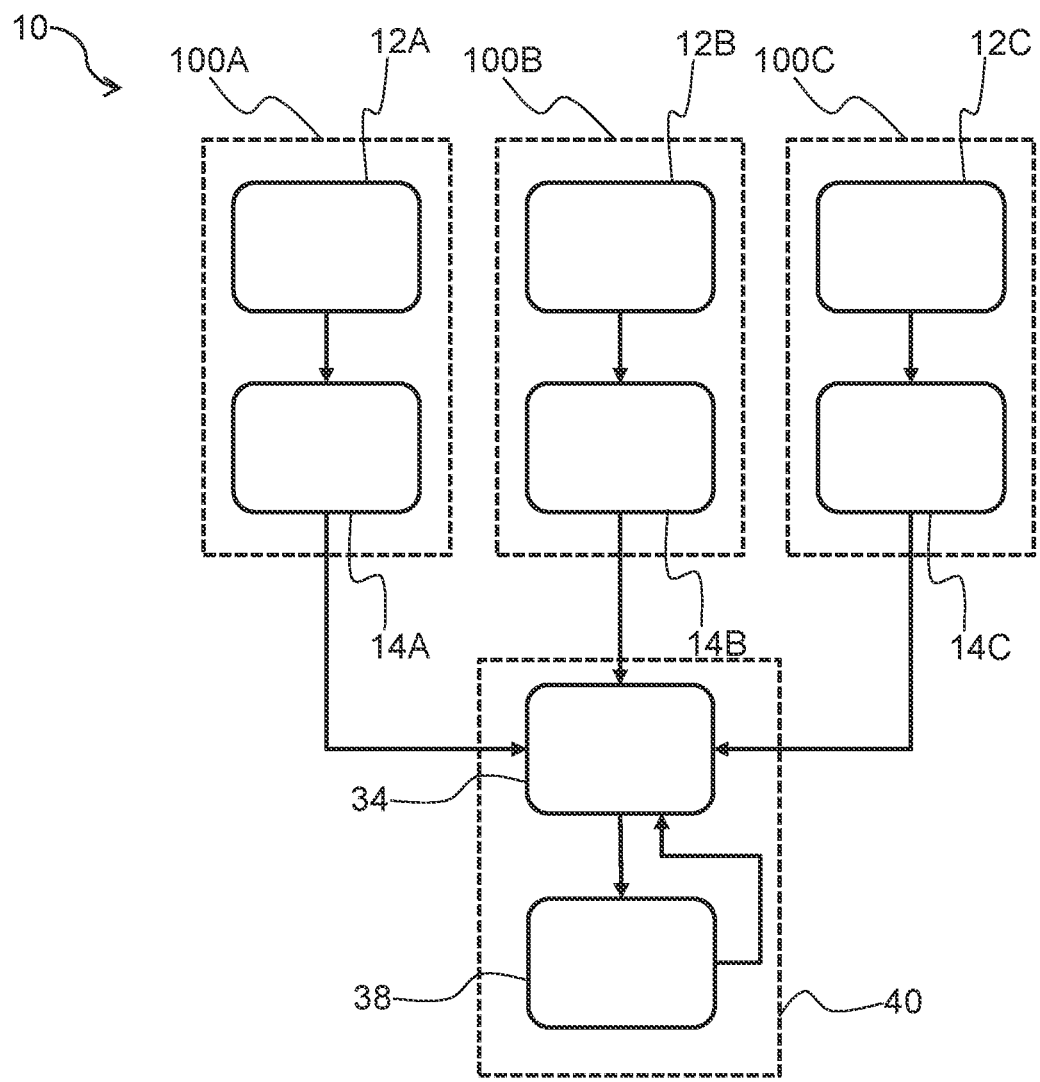
FIG. 3 is a block diagram of an example system.

FIG. 3 shows a block diagram of a system 10 according to a non-limiting example. The system 10 may, for example, be alternatively termed "an inhaler assembly".

As shown in FIG. 3, the system 10 comprises a first inhaler 100A comprising a first use determination system 12A and a first transmission module 14A. The system 10 further comprises a second inhaler 100B comprising a second use determination system 12B and a second transmission module 14B. The first inhaler 100A delivers a first medicament, and the second inhaler 100B delivers a second medicament which in some examples is different from the first medicament, as previously described.

Whilst not essential in the context of the present disclosure, the system 10 depicted in FIG. 3 further comprises a third inhaler 100C comprising a third use determination system 12C, and a third transmission module 14C. The third inhaler 100C delivers a third medicament which is different from the first and second medicaments. In other examples, no third inhaler 100C is included in the system 10, or a fourth, fifth, etc. inhaler (not visible) is included in addition to the first inhaler 100A, the second inhaler 100B, and the third inhaler 100C. Alternatively or additionally, the system 10 includes a plurality of first inhalers 100A, a plurality of second inhalers 100B, and so on, as previously described.

The system 10 comprises a processing module 34 which is configured to receive the respective encrypted data transmitted from each of the transmission modules 14A, 14B, 14C, as represented in FIG. 3 by the arrows between each of the blocks corresponding to the transmission modules 14A, 14B, 14C and the block corresponding to the processing module 34. The first, second, and/or third encrypted data may be transmitted wirelessly to the processing module 34, as previously described. The processing module 34 may thus comprise a suitable receiver or transceiver for receiving the encrypted data. The receiver or transceiver of processing module 34 may be configured to implement the same communication protocols as transmission modules 14A, 14B, 14C and may thus include similar communication hardware and software as transmission modules 14A, 14B, 14C as described herein (not shown in FIG. 3).

The processing module 34 may comprise a suitable processor and memory configured to perform the functions described herein for the processing module. For example, the processor may be a general purpose processor programmed with computer executable instructions for implementing the functions of the processing module. The processor may be implemented using a microprocessor or microcontroller configured to perform the functions of the processing module. The processor may be implemented using an embedded processor or digital signal processor configured to perform the functions of the processing module. In an example, the processor may be implemented on a smartphone or other consumer electronic device that is capable of communicating with transmission modules 14A, 14B, 14C and performing the functions of the processing module 34 as described herein. For example, the processing module may be implemented on a user device, such as a smart phone or consumer electronic device, that includes an application (e.g., a mobile application) that causes the processor of the user device to perform the functions of the processing module 34 as described herein.

The processing module 34 distinguishes between the first encrypted data, the second encrypted data, and the third encrypted data, for example by using respective identifiers, as previously described.

The processing module 34 determines first usage information relating to the first medicament based on the distinguished first encrypted data. The first usage information may comprise a registered use of, or inhalation performed using, the first inhaler 100A, and/or a parameter relating to airflow during such an inhalation using the first inhaler 100A, as previously described. The usage information may include the usage parameter or information derived from the usage parameter. And in some examples, the usage parameter may be a usage event.

Similarly, the processing module 34 determines second and third usage information relating to the second and third medicaments respectively, based on the distinguished second and third encrypted data.

The system 10 further comprises a user interface 38. The processing module 34 is configured to control the user interface 38 to communicate the first, second, and/or third usage information. The arrow pointing from the block representing the processing module 34 to the block representing the user interface 38 is intended to represent the control signal(s) which causes or cause the user interface to communicate, for example display, the respective usage information. In this respect, the user interface 38 may comprise any suitable display, screen, for example touchscreen, etc. which is capable of displaying the respective usage information. Alternatively or additionally, the respective usage information may be provided by the user interface 38 via an audio message. In such an example, the user interface 38 comprises a suitable loudspeaker for delivering the audio message. Numerous ways of communicating the respective usage information can be used.

The system 10 thus enables the subject to be informed of their usage of the respective medicaments, which may be administered according to a treatment regimen and/or an administration protocol specific to the respective medicament, as previously described.

Whilst the transmission modules 14A, 14B, 14C are each shown in FIG. 3 as transmitting (encrypted) data to the processing module 34, this is not intended to exclude the respective inhalers 100A, 100B, 100C, or a component module thereof, receiving data transmitted from the processing module 34.

In a non-limiting example, a clock module (not visible in the Figures) is included in each of the respective inhalers 100A, 100B, 100C for assigning a time, for example a time stamp, to the usage parameter of the respective inhaler 100A, 100B, 100C. In this example, the processing module 34 is configured to synchronize the clock modules of the respective inhalers 100A, 100B, 100C. Such synchronization may, for instance, provide a point of reference which enables the relative timing of use of the respective inhalers 100A, 100B, 100C to be determined, which may have clinical relevance, as previously described. The assigned time, for example time stamp, may, for instance, be included in the usage information for the respective medicaments communicated, e.g. displayed, by the user interface 38.

Whilst not shown in FIG. 3, the processing module 34 may, in some examples, comprise a further clock module. The clock modules of each of the respective inhalers 100A, 100B, 100C may thus be synchronized according to the time provided by the further clock module. The further clock module may, for instance, receive the time of the time zone in which the processing module 34 is situated. This may cause the respective inhalers 100A, 100B, 100C to be synchronized according to the time in which the subject and their respective inhalers 100A, 100B, 100C are located, which may provide further information of clinical relevance, as previously described.

In an embodiment, the processing module 34 is at least partly included in a first processing module included in the user device 40. By implementing as much processing as possible of the usage data from the respective inhalers 100A, 100B, 100C in the first processing module of the user device 40, battery life in the respective inhalers 100A, 100B, 100C may be advantageously saved. The user device 40 may be, for example, at least one selected from a personal computer, a tablet computer, or a smart phone. And in some examples, the processing module 34 may include (e.g., be) a mobile application residing on the user device 40.

Alternatively or additionally, the user interface 38 may be at least partly defined by a first user interface of the user device 40. The first user interface of the user device 40 may, for instance, comprise, or be defined by, the touchscreen of a smart phone 40.

In other non-limiting examples, the processing module is not included in a user device. The processing module (or at least part of the processing module 34) may, for example, be provided in a server, e.g. a remote server such as the DHP.

FIG. 4 shows front and rear views of the exterior of an inhaler 100 according to a non-limiting example. The inhaler 100 comprises a top cap 102, a main housing 104, a mouthpiece 106, a mouthpiece cover 108, and an air vent 126. The mouthpiece cover 108 may be hinged to the main housing 104 so that it may open and close to expose the mouthpiece 106 and the air vent 126. The depicted inhaler 100 also comprises a mechanical dose counter 111, whose dose count may be used to check the number of doses remaining as determined by the processing module (on the basis of the total number of doses contained by the inhaler 100 prior to use and on the uses determined by the use determination system 12), as previously described.

In the non-limiting example shown in FIG. 4, the inhaler 100 has a barcode 42 printed thereon. The barcode 42 in this example is a quick reference (QR) code printed on the uppermost surface of the top cap 102. The use determination system 12 and/or the transmission module 14 may, for example, be located at least partly within the top cap 102, for example as components of an electronics module (not visible in FIG. 4). The electronics module of the inhaler 100 will be described in greater detail with reference to FIGS. 12 to 15.

The QR code is more clearly visible in FIG. 5, which provides a view from directly above the top cap 102 of the inhaler 100 shown in FIG. 4. The QR code 42 may provide a facile way of pairing the respective inhaler 100 with the processing module 34, in examples in which the user device 40 comprises a suitable optical reader, such as a camera, for reading the QR code. FIG. 6 shows a user pairing the inhaler 100 with the processing module 34 using the camera included in the user device 40, which in this particular example is a smart phone.

Such a bar code 42, e.g. QR code, may comprise the identifier which is assigned to the respective medicament of the inhaler 100, as previously described. Table 1 provides a non-limiting example of the identifiers included in the QR code 42 for various inhalers 100.

TABLE 1

| Identifier in QR code | Brand of inhaler | Medicament | Dose strength (mcg) | Total dose count of inhaler prior to use | Medicament identification number |
|---|---|---|---|---|---|
| <blank> | ProAir Digihaler | albuterol | 117 | 200 | AAA200 |
| AAA030 | ProAir Digihaler | albuterol | 117 | 30 | AAA030 |
| FSL060 | AirDuo Digihaler | fluticasone/ salmeterol | 55/14 | 60 | FSL060 |
| FSM060 | AirDuo Digihaler | fluticasone/ salmeterol | 113/14 | 60 | FSM060 |
| FSH060 | AirDuo Digihaler | fluticasone/ salmeterol | 232/14 | 60 | FSH060 |
| FPL060 | ArmonAir Digihaler | fluticasone | 55 | 60 | FPL060 |
| FPM060 | ArmonAir Digihaler | fluticasone | 113 | 60 | FPM060 |
| FPH060 | ArmonAir Digihaler | fluticasone | 232 | 60 | FPH060 |

As shown in Table 1, the identifier further denotes the dose strength and the total dose count of the inhaler prior to use. The processing module 34 may use the former to, in combination with the usage information, control the user interface 38 to issue a notification when the label recommended dosages have been exceeded, as previously described. Alternatively or additionally, the processing module 34 may use the total dose count of the inhaler prior to use and the usage information to determine the number of doses remaining in the respective inhaler 100, as previously described.

The barcode 42, e.g. QR code, on the inhaler may, for instance, further comprise a security key, for example in the form of a series of alphanumerical characters, for preventing unauthorized users from accessing the respective inhaler 100. The processing module 34 may be able to decrypt the respective encrypted data once the processing module 34 has been provided with the security key, but may not be able to decrypt the respective encrypted data before the processing module 34 has been provided with the security key. More generally, the security key may be included in the respective identifier.

In a non-limiting example, the system is configured to restrict one or more, e.g. each, of the inhalers included in the system to a single user account.

In such an example, a passkey, e.g. provided in the QR code, may allow synchronization between the respective inhaler and the processing module of the system. The passkey and, in turn, the usage parameter data, e.g. inhalation and/or usage data, from the respective inhaler may be public. This public inhalation data may not be associated with the particular subject until synchronization with the single user account.

Since the system is configured to restrict the respective inhaler to being associated with the single user account, the respective inhaler may be prevented from being synchronized with another user account, for example in situations where the inhaler is lost or stolen. In this way, third parties may be prevented from acquiring usage parameter data which is not theirs.

In other non-limiting examples, the processing module 34 may be paired with the respective inhaler 100 by, for example, manual entry of an alphanumerical key including the respective identifier via the user interface, e.g. a touch-screen.

Figure 7:
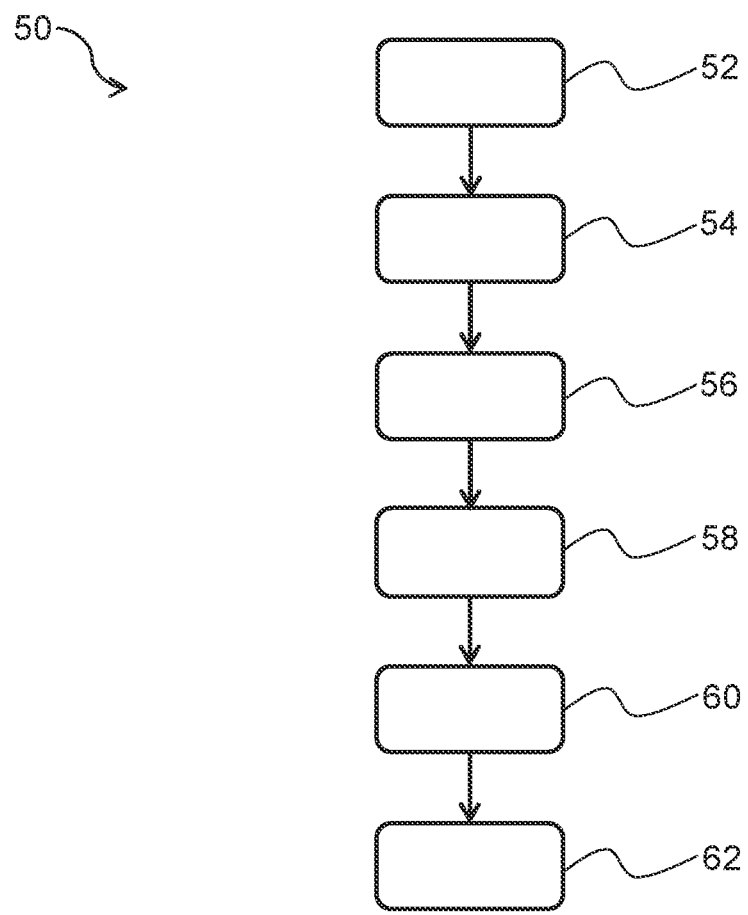
FIG. 7 is a flowchart of a method according to an example.

FIG. 7 is a flowchart of a method 50 according to an example. The method 50 comprises receiving 52 first encrypted data from a first transmission module of a first inhaler configured to deliver a first medicament to a subject. The first encrypted data is based on a first value of a usage parameter relating to use of the first inhaler determined by a first use determination system included in the first inhaler, as previously described.

Second encrypted data is received 54 from a second transmission module included in a second inhaler configured to deliver a second medicament to the subject. The second encrypted data is based on a second value of a usage parameter relating to use of the second inhaler. The second medicament is different from the first medicament;

The method further comprises distinguishing 56 between the first encrypted data and the second encrypted data, and determining 58 first usage information relating to the first medicament from the distinguished first encrypted data. Second usage information relating to the second medicament is determined 60 from the distinguished second encrypted data. A user interface is controlled 62 to display the first and second usage information. As one non-limiting examples, the user interface may display a GUI that displays the first and second usage information, for example, simultaneously in a single GUI.

In an embodiment, the receiving 52 the first encrypted data comprises receiving the first encrypted data from each respective first transmission module of a plurality of first inhalers, each of said plurality of first inhalers being configured to deliver the first medicament.

Alternatively or additionally, the receiving 54 the second encrypted data may comprise receiving the second encrypted data from each respective second transmission module of a plurality of second inhalers, each of said plurality of second inhalers being configured to deliver the second medicament.

Whilst not shown in FIG. 7, the method 50 may further comprise receiving third encrypted data from a third transmission module included in a third inhaler configured to deliver a third medicament which is different from the first and second medicaments. In such an example, the method 50 comprises distinguishing the third encrypted data from the first encrypted data and the second encrypted data, and determining third usage information relating to the third medicament from the distinguished third encrypted data. The user interface is controlled to display the third usage information.

The method 50 may comprise receiving identifiers, each identifier being assigned according to the medicament which is delivered by the respective inhaler. The respective identifiers may then be used to distinguish 56 the respective encrypted data, as previously described.

A clock module may, for instance, be included in each of the respective inhalers for assigning a time to said usage parameter of the respective inhaler. In such an example, the method 50 further comprises synchronizing the clock modules of the respective inhalers. The time assigned to the usage parameter may, for example, be included in the usage information for the respective medicaments. The synchronizing may in some examples comprise synchronizing each of the respective clock modules with the time of the time zone in which the respective inhalers are situated, as previously described.

In a non-limiting example, the processing module determines a use and/or system error based on the encrypted data received from one or more, e.g. each, of the inhalers included in the system. A use and/or system error may be a type of usage event. Such a use error may, for example, be indicative of potential misuse of the respective inhaler or inhalers. The system error may be indicative of a fault with a component of the respective inhaler, such as the use determination system and/or the transmission module of the respective inhaler. A system error may, for example, include a hardware fault of the respective inhaler. The user interface may be controlled by the processing module to provide an alert or notification based on the determined use and/or system error (e.g., such as providing an alert or notification for the determined use and/or system errors of each of a plurality of different inhalers, potentially including different medicaments).

A use error may, for example, include a low inhalation event, a no inhalation event, and/or an excessive inhalation event. Such events will be described in more detail below with reference to FIG. 16.

A use error may alternatively or additionally include one or more of: the mouthpiece cover being left open for more than a predetermined time period, e.g. 60 seconds; multiple inhalations being recorded in respect of a single actuation of the above-described mechanical switch, for example a second inhalation performed within the same mouthpiece cover open/closed session; and an exhalation through the flow pathway, as determined from a positive pressure change being sensed in the flow pathway.

When the use error relates to the mouthpiece cover being left open for more than the predetermined time period, the inhaler's detection circuitry may only stay active for the predetermined time period to preserve battery life. This may mean that anything which would otherwise be detectable/determinable by the use determination system that occurs outside of this predetermined time period is not detected/recorded. Notifying the user of this error may therefore serve the purpose of informing the user that otherwise detectable events are not detected outside the predetermined time period triggered by opening of the mouthpiece cover.

It is noted that the abovementioned exhalation-based use error may not be recorded if such an exhalation is sensed subsequently to an inhalation being performed in respect of a given actuation of the mechanical switch, e.g. within the same mouthpiece cover open/closed session.

System errors may include one or more of: a problem occurring when saving inhalation data to a memory included in the inhaler, such as a memory included in the use determination system ("corrupted data error"); an error with the clock module of the inhaler ("time stamp error"); and an error relating to collecting information about the inhalation ("inhalation parameter error").

In a particular example, use and/or system errors from more than one, e.g. all of, the inhalers included in the system are collected, e.g. aggregated, by the processing module. The processing module is further configured to control the user interface to provide the alert or notification based on the collected use and/or system errors. For instance, the processing module controls the user interface to provide the alert or notification based on the number of use and/or system errors collected from the inhalers included in the system reaching or exceeding a predetermined number of use and/or system errors.

Figure 8:
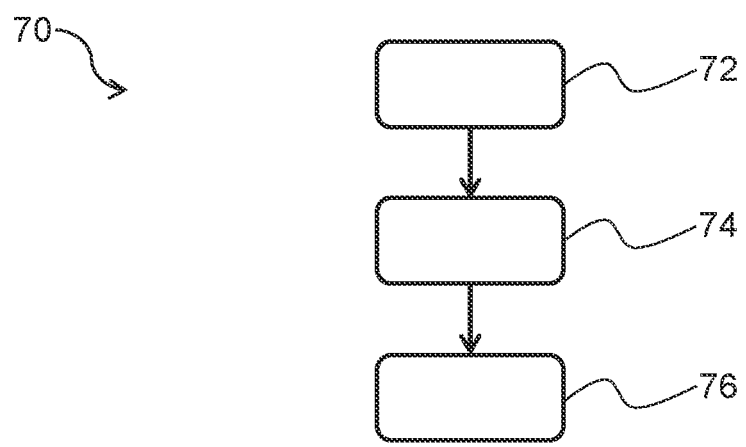
FIG. 8 is a flowchart of a method according to another example.

As shown in FIG. 8, the present disclosure further provides a method 70 comprising adding 72 a further inhaler configured to dispense a medicament to a system comprising a processing module, a user interface, and an existing inhaler which is also configured to dispense the medicament. The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The method 70 comprises receiving 74 an identifier provided with the further inhaler, for example via a barcode, such as a QR code, printed on the further inhaler or its packaging, as previously described. The identifier denotes at least the medicament and the dose strength of the medicament. The method further comprises using 76 the processing module to control the user interface to issue at least one notification if the dose strength of the medicament in the further inhaler as denoted by the identifier is different from the dose strength of the medicament in the existing inhaler.

The at least one notification may, for example, comprise a notification informing the subject that the dose strength of the further inhaler is different from that of the existing inhaler and/or a notification to request that the subject discards the existing inhaler. In this manner, the system may assist the subject to adjust to a prescription change.

The present disclosure further provides a method comprising determining whether a medicament of a further inhaler which is added to a system, which system comprises a processing module, a user interface, and an existing inhaler which delivers a maintenance medicament, is a further maintenance medicament.

The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The determination of whether the medicament is a further maintenance medicament may, for example, be based on an identifier which identifies that the further medicament is a maintenance medicament or is a different medicament type, such as a rescue medicament. The identifier may be received by the processing module of the system, and the processing module may implement the determination. Such an identifier may, for example, be included in a QR code of the further inhaler, as previously described.

If the medicament is identified as a further maintenance medicament, the method may further comprise controlling the user interface to prompt the user to select one of the existing inhaler and the further inhaler. Reminders may then be issued, e.g. by the processing module controlling the user interface to provide such reminders, according to the user selection to remind the subject to use the existing inhaler or the further inhaler according to a treatment regimen relating to administering of the maintenance medicament or the further maintenance medicament respectively.

In this manner, the method (or the system which is configured to implement the method) may limit such reminders to one maintenance inhaler. In other words, for instances where the subject is prescribed multiple maintenance inhalers, the user selection may cause the system to provide reminders for the selected maintenance inhaler, but not provide reminders for the maintenance inhaler which was not selected. The subject or user may select the particular maintenance inhaler based on the specific or current treatment regimen of the subject.

Alternatively or additionally, the method may comprise, based on the determination that the medicament is a further maintenance medicament, providing an alert, e.g. via the user interface and/or by transmitting a notification to a healthcare provider, that the system comprises both the maintenance medicament and the further maintenance medicament.

Such an alert may, for example, comprise a message informing the user or subject to verify with their healthcare provider (and/or doctor) that a plurality of maintenance medicaments are prescribed for the subject.

Such an example may be applicable when, for instance, the subject is prescribed two maintenance medicaments at the same time, e.g. when the subject is transitioning between maintenance treatments. When the further inhaler is added to the system, for example when the QR code of the further inhaler is scanned, the processing module may be configured to provide the alert, e.g. by controlling the user interface and/or by transmitting the alert to the subject's healthcare provider.

Also provided is a computer program comprising computer program code which is adapted, when the computer program is run on a computer, to implement any of the above-described methods. In a preferred embodiment, the computer program takes the form of an app, for example an app for a user device 40, such as a mobile device, e.g. tablet computer or a smart phone.

Figure 9:
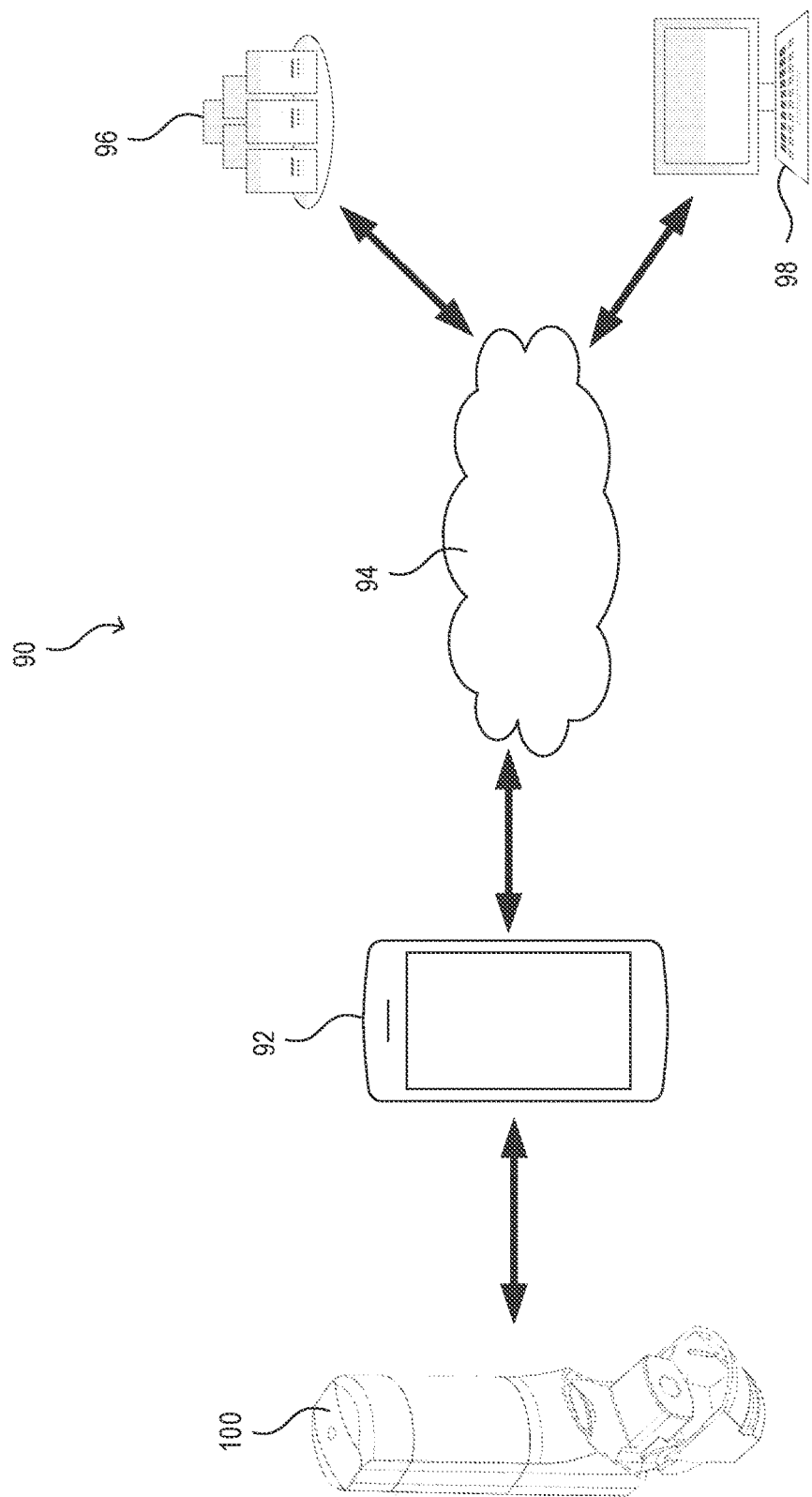
FIG. 9 is a diagram of an example system including the inhalation device.

FIG. 9 is a diagram of an example system 90 including the inhalation device 100, a user device 92 comprising a processing module (e.g., a user device comprising a mobile application), a public and/or private network 94 (e.g., the Internet, a cloud network, etc.), a computer or server 98 associated with a health care provider, such as a hospital or hospital system, a health system, a medical group, a physician, a clinic, and/or a pharmaceutical company. The system 90 also includes a digital health platform (DHP) 96 that resides on one or more servers, and may include computer software configured to perform the functions described in relation to the DHP 96.

The user device 92 may include a smart phone (e.g., an iPhone® smart phone, an Android® smart phone, or a Blackberry® smart phone), a personal computer, a laptop, a wireless-capable media device (e.g., MP3 player, gaming device, television, a media streaming device (e.g., the Amazon Fire TV, Nexus Player, etc.), etc.), a tablet device (e.g., an iPad® hand-held computing device), a Wi-Fi or wireless-communication-capable television, or any other suitable Internet-Protocol-enabled device. For example, the user device 92 may include a transmission module, as described herein, and as such may be configured to transmit and/or receive RF signals via a Wi-Fi communication link, a Wi-MAX communications link, a Bluetooth® or Bluetooth Smart communications link, a near field communication (NFC) link, a cellular communications link, a television white space (TVWS) communication link, or any combination thereof. The user device 92 may transfer data through the public and/or private network 94 to the DHP 96 using, for example, a dedicated API. For example, the user device 92 may send usage data relating to one or more inhalers to the DHP 96.

The user device 92 may process and analyze the data to determine the usage parameters associated with the inhalation device 100. For example, the user device 92 may process the data to identify usage events, such as no inhalation events, low inhalations events, good inhalation events, excessive inhalation events, exhalation events, actuation events, error events, underuse events, overuse events, etc.

The user device 92 include a display device and software for visually presenting the usage parameters and/or data related to usage events through a GUI on the display device.

The DHP 96 is configured to receive and aggregate data from inhalers 100 that are associated with a plurality of different users. For example, the DHP 96 is configured to receive and store inhaler data from processing modules residing on user devices (e.g., the patient-facing mobile applications). The DHP 96 is configured to analyze and manipulate the data. Further, the DHP 96 is also configured to provide data to the computer 98 associated with a health care provider (e.g., via the dashboard application). The inhaler data may include any of the data described with reference to the inhalers described herein.

The inhaler data may be associated with an inhaler 100 and/or a user profile, for example, at the processing module (e.g., residing on the user device 92) and/or at the DHP 96. One user profile may be associated with multiple inhalers 100 of the same and/or different medicament types. The DHP 96 may also de-identify (e.g., unassociate) the inhaler data with a particular user profile, and the DHP 96 may perform analytics on de-identified data relating to the inhalers 100. Although described as receiving the inhaler data from the processing modules 92, in some examples, the DHP 96 may receive the data directly from the inhalers 100 themselves, such as in instances where the transmission modules on the inhalers 100 include cellular chipsets that are capable of communicating directly with the DHP 96.

The DHP 96 may be configured to enable, and in some instances initiate, the transfer of data from the processing modules residing on user devices 92. For example, the DHP 96 may expose a REST API to the processing modules residing on the user devices 92. The DHP 96 may also store incoming data from the computers 98. The DHP 96 may receive the patient's consent via their respective processing module residing on their user device 92.

The DHP 96 may include a dashboard application that may be accessible by the computer 98 associated with a health care provider. In some examples, the dashboard application is a web application (e.g., a web portal). For example, the DHP 96 is configured to provide data, such as inhaler data, to clinicians and physicians through the use of the dashboard application (e.g., via a REST API).

Figure 10:
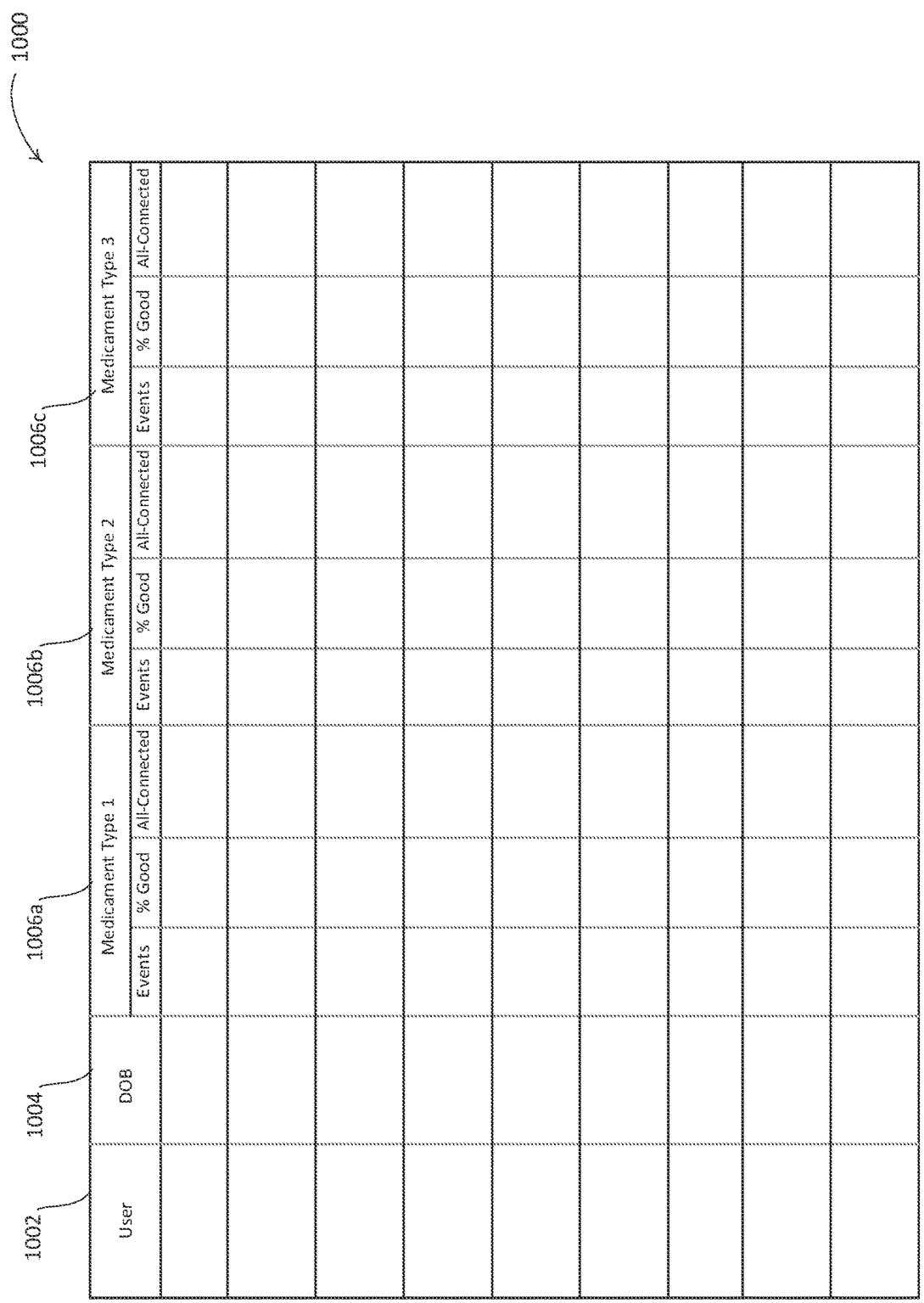
FIG. 10 is a first view of a user interface according to an example.

The DHP 96 may cause the computer 98 associated with the health care provider to provide inhaler data to practitioners and health care professionals to allow them to view inhaler data specific to a program to which a patient has consented. In one example, the DHP 96 causes the computer 98 associated with the health care provider to provide the inhalation data via a graphical user interface (GUI) that is presented on the health care provider's computer. One non-limiting example GUI 1000 is illustrated in FIG. 10, which may be the portion of an entire GUI that is displayed on a display device associated with the computer 98. Each GUI may be, for example, specific for a particular program (as described above), and may provide any combination of the name of the users 1002 (e.g., patients), the date-of-birth of the users 1004, and inhaler data 1006a-n that is divided in columns for each specific medicament type that is part of the program. The GUI 1000 may provide specific information for each user, and for example, the information may be aggregated by medicament type for all of the user's inhalers 100 that provide a particular medicament type. For instance, the GUI may provide a total number of usage events (e.g., inhalation events, such as, good inhalation events, fair inhalation events, low or no inhalation events, exhalation events, and possible air vent block events) that have occurred over a period of time, such as one week or 30 days, for all inhalers 100 that include a particular medicament type, a percentage of the inhalation events that are categorized as good inhalation events, and an all-connected duration that represents the oldest, or least recent, last synchronization time of the inhalers 100 of a particular medication type that are associated with the user.

Further, in some example, the DHP 96 is configured to prioritize the listing of users on the GUI based on the particular medicaments that are included in the program. For instance, as noted above, the DHP 96 may be configured to prioritize the listing of users on the GUI to first indicate those users with the highest number of usage events (e.g., over a particular time range, such as one week) of inhalers 100 that include a rescue medicament type, when the rescue medicament type and the maintenance medicament type are included in the program. In such examples, the DHP 96 is also configured to prioritize the listing of users on the GUI to first indicate those users with the lowest number of usage events (e.g., over a particular time range, such as one month) of inhalers 100 that include the maintenance medicament type when the rescue medicament type is not included in the program.

Figure 11:
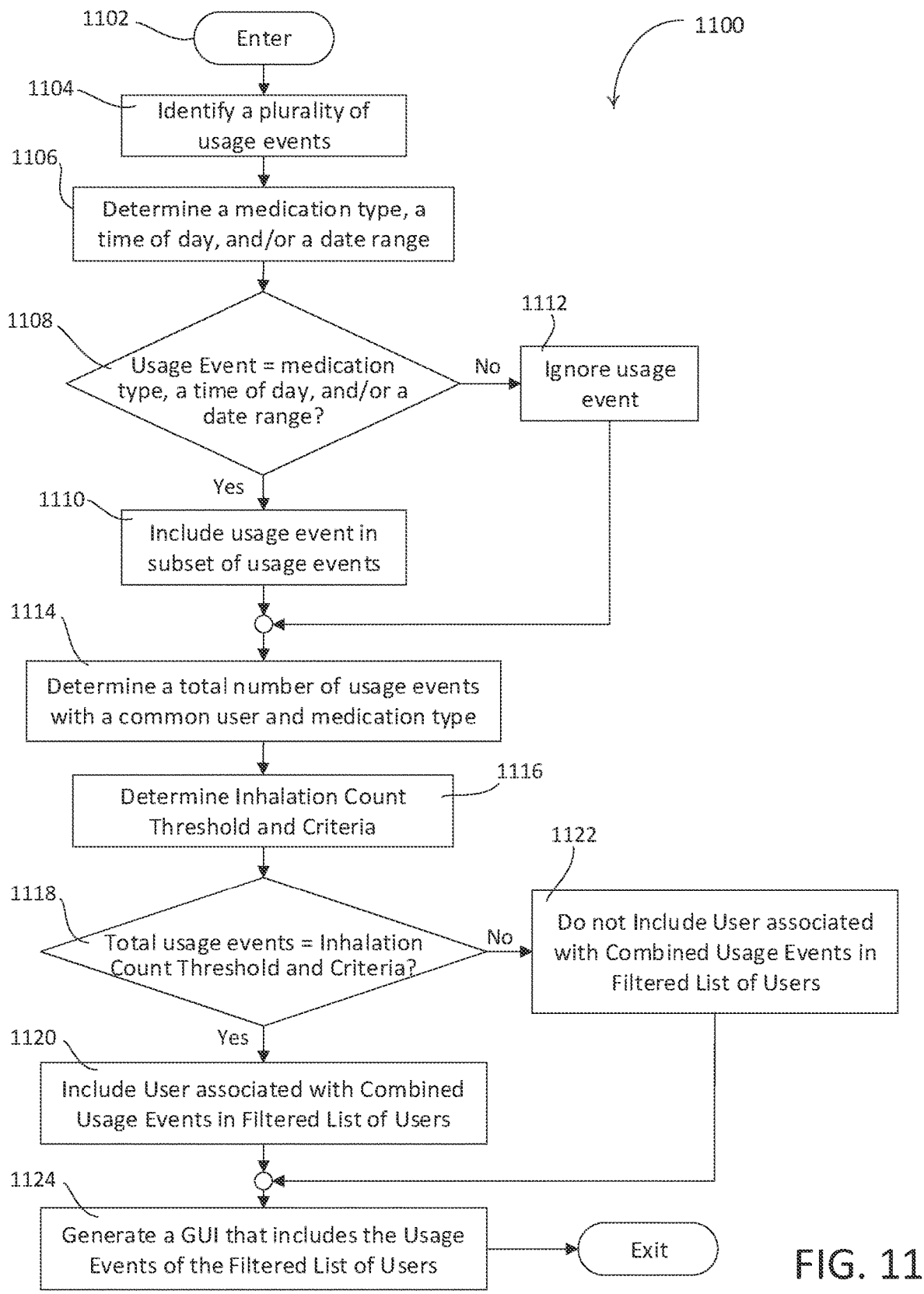
FIG. 11 is a flowchart of a procedure performed by a DHP to generate a reduced set of users.

FIG. 11 is a flowchart of a procedure 1100 performed by a DHP. The DHP may perform the procedure 1100 automatically in response to receiving a user request and/or in response to receiving new usage events. The procedure 1100 may begin at 1102. At 1104, the DHP may identify a plurality of usage events. For example, the DHP may identify the usage events based on a program, a physician, an organization, or the like. As noted above, a program may define a set of criteria, such as types of medications (e.g., any combination of rescue and/or maintenance medications), specific patients and in turn their applicable inhalers (e.g., based on medication type), other users of the programs such as particular physicians, practice groups, and/or administrators, the types of data presented to the health care provider such as charts, event tables, usage summaries, etc. As such, the plurality of usage events may be those usage events that associated with a program, a physician, and/or organization.

At 1106, the DHP may identify a medication type(s), a time of day, and/or a date range. The medication type(s) may include one or more rescue medication types and/or one or more maintenance medication types. The time of day may include, for example, daytime (e.g., defined as between 8 am and 8 pm), nighttime (e.g., defined as between 8 pm and 8 am), and all day. Alternatively or additionally, time of day may include a customizable definition of a time period, such as between a start time (e.g., 10 pm) and an end time (e.g., 6 am). The date range may include a start and end date, or may include a selection of a preconfigured, dynamically adjusted date range, such as the last week(s), last month, etc. In some examples, the DHP may receive a selection (e.g., from a user) of a medication type(s), a time of day, and/or a date range. In other examples, the DHP may run computer logic to determine the medication type(s), the time of day, and/or the date range.

At 1108, the DHP may determine a subset of the usage events based on the selected medication type, the selected time of day, and/or the selected date range. The DHP may compare each usage event of the plurality of usage events to the selected medication type, the selected time of day, and/or the selected date range. If the usage event matches the selected medication type, the selected time of day, and the selected date range, the DHP may include the usage event in a defined subset of usage event at 1110. If not, the DHP may ignore the usage event at 1112. As such, and for example, the DHP may apply a usage event filter to filter the plurality of usage events received from a plurality of different inhalers to determine a subset of usage events based on the selected medication type, the selected time of day, and/or the selected date range. The DHP may repeat 1108-1112 for each usage event of the plurality of usage events.

At 1114, the DHP may determine a total number of usage events, out of the subset of usage events (e.g., determined at 1110) with a common user and medication type. As such, the DHP may determine a number of usage events out of the subset of usage events that are associated with the same user and medication type. For example, the DHP may associate (e.g., group or combine) usage events out of the subset of usage events that have a common user and medication type.

At 1116, the DHP may determine an inhalation count threshold and criteria. For example, the DHP may receive a selection of the inhalation count threshold, for instance, from a user. The inhalation count threshold may be a number. In some examples, the inhalation count threshold may be determined based on a different, non-overlapping subset of the usage events that are associated with the same user and medication type. For instance, the different, non-overlapping subset of usage events is associated with a different date range than the number of usage events, but is associated with the same medication type and time of day. The criteria may, for example, include any of less than, greater than, less than or equal to, greater than or equal to, proportionally greater than (e.g., at least 50% greater than), and/or proportionally less than (e.g., at least 50% less than).

The DHP may determine a filtered list of users out of the plurality of users based on a comparison of the selected inhalation count threshold with the number of usage events that are associated with the same user and medication type. At 1118, the DHP may determine whether the total number of usage events with a common user and medication type meet the inhalation count threshold and the criteria. The criteria may be, in some example, selected by a user or determined based on analytics. So, as an example, if the inhalation count threshold is five and the criteria is greater than, the DHP may determine whether the total number of usage events with a common user and medication type is greater than five. If the combined usage events do meet the inhalation count threshold and criteria, the DHP may include the user associated with the combined usage events in the filtered list of users at 1120. However, if the combined usage events do not meet the inhalation count threshold and the criteria, the DHP may not include the user associated with the combined usage events in the filtered list of users at 1122. For example, the DHP may ignore (e.g., discard) the user and their associated usage events. The DHP may conduct 1118 for each unique combination of user and medication type that includes at least one usage event in the subset of usage events. At 1124, the DHP may generate a GUI (e.g., via a display device of a remote computer terminal) that comprises the number of usage events for each user of the filtered list of users.

Accordingly, the DHP may generate a filtered set of users by performing the procedure 1100 by analyzing and manipulating the digital data received from a vast number of digital inhaler systems to generate a subset or filtered list of users and/or inhalers that, for example, present a health care provider with those users and/or medication types that are indicative of patients who are high risk and/or poor adherence or compliance with their treatment regimen. For instance, the DHP may be configured to generate a filtered list of users based on the plurality of usage events and one or more variables.

Further, in some example, the DHP may be configured to compare different subsets of usage events to one another, where for instance, the different subsets of usage events may be associated with the same users. For example, at 1118-1120, the DHP may determine whether the number (e.g., the total number) of usage events that are associated with the same user and medication type of a first subset of usage events is proportionally smaller than or proportionally greater than the number (e.g., the total number) of a different, non-overlapping subset of the usage events that are associated with the same user and medication type (e.g., instead of the processes described with respect to 1118-1120 in FIG. 11). In some instances, the different, non-overlapping subset of usage events is associated with a different date range than the number of usage events, but is associated with the same medication type and time of day. For example, the DHP may be configured to determine the users out of the subset of users who had more than X % increase (e.g., 50% increase) in usage events over a period of time (e.g., this week) for a particular medication type (e.g., a rescue medication type) as compared to a different time period (e.g., the previous week). As another example, the DHP may be configured to determine the users out of the subset of users who had more than an X % decrease (e.g., 50% decrease) in usage events over a period of time (e.g., this week) for a particular medication type (e.g., a maintenance medication type) as compared to a different time period (e.g., the previous week). This analysis will, for example, help health care providers quickly and easily identify those users who are at risk and/or exhibiting a decrease in the adherence or compliance to their treatment regimen.

FIGS. 12-15 provide a non-limiting example of an inhaler arrangement 100 which may be included in the system 10.

Figure 12:
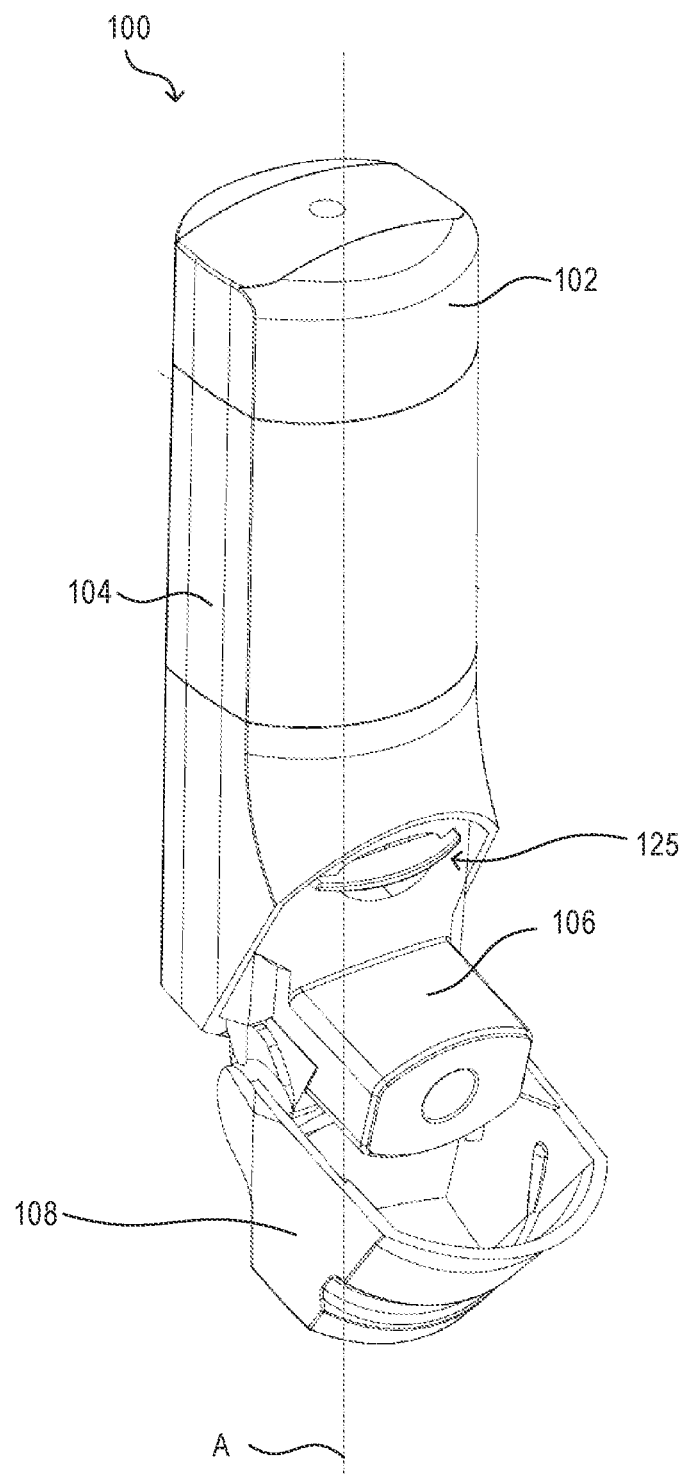
FIG. 12 is a front perspective view of an exemplary inhaler.

FIG. 12 provides a front perspective view of an inhaler arrangement 100, referred to as "an inhaler" from here on, according to a non-limiting example. The inhaler 100 may, for example, be a breath-actuated inhaler. The inhaler 100 may include a top cap 102, a main housing 104, a mouthpiece 106, a mouthpiece cover 108, an electronics module 120, and an air vent 126. The mouthpiece cover 108 may be hinged to the main housing 104 so that it may open and close to expose the mouthpiece 106. Although illustrated as a hinged connection, the mouthpiece cover 106 may be connected to the inhaler 100 through other types of connections. Moreover, while the electronics module 120 is illustrated as housed within the top cap 102 at the top of the main housing 104, the electronics module 120 may be integrated and/or housed within the main body 104 of the inhaler 100.

The electronics module 120 may, for instance, include the above-described use determination system 12 and the transmission module 14. For example, the electronics module 120 may include a processor, memory configured to perform the functions of use determination system 12 and/or transmission module 14. The electronics module 120 may include switch(es), sensor(s), slider(s), and/or other instruments or measurement devices configured to determine inhaler usage information as described herein. The electronics module 120 may include a transceiver and/or other communication chips or circuits configured to perform the transmission functions of transmission module 14. Although shown as integrated into the inhalation device 100, in some examples, the electronics module 120 may be removable and replaceably attachable to an inhalation device.

Figure 13:
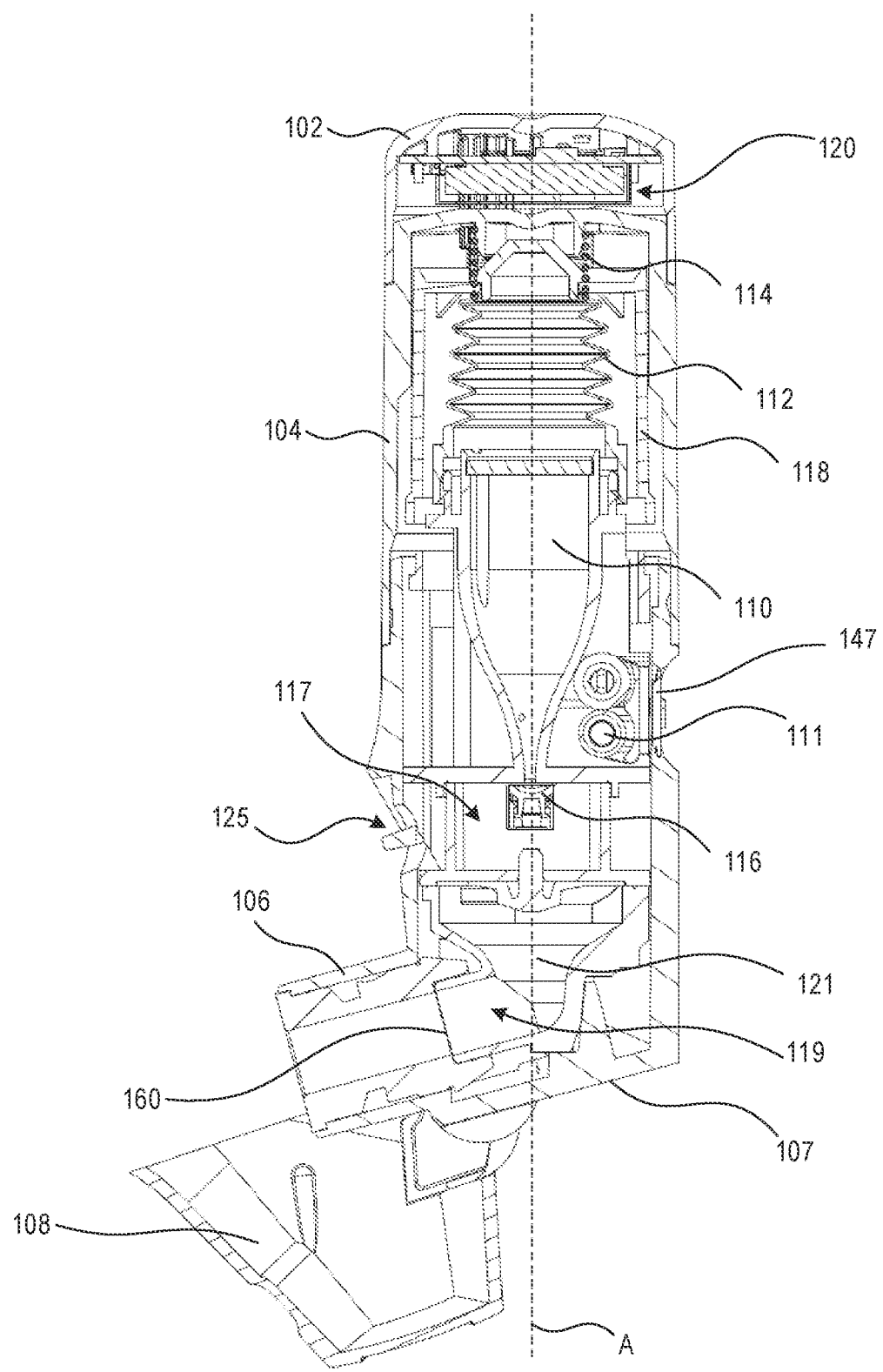
FIG. 13 is a cross-sectional interior perspective view of the inhaler shown in FIG. 12.

FIG. 13 provides a cross-sectional interior perspective view of the example inhaler 100. Inside the main housing 104, the inhalation device 100 may include a medication reservoir 110 and a dose metering assembly. For example, the inhaler 100 may include a medication reservoir 110 (e.g. a hopper), a bellows 112, a bellows spring 114, a yoke (not visible), a dosing cup 116, a dosing chamber 117, a deagglomerator 121, and a flow pathway 119. The medication reservoir 110 may include medication, such as dry powder medication, for delivery to the subject. Although illustrated as a combination of the bellows 112, the bellows spring 114, the yoke, the dosing cup 116, the dosing chamber 117, and the deagglomerator 121, the dose metering assembly may include a subset of the components described and/or the inhalation device 100 may include a different dose metering assembly (e.g., based on the type of inhalation device, the type of medication, etc.). For instance, in some examples the medication may be included in a blister strip and the dose metering assembly, which may include one or more wheels, levers, and/or actuators, is configured to advance the blister strip, open a new blister that includes a dose of medication, and make that dose of medication available to a dosing chamber and/or mouthpiece for inhalation by the user.

When the mouthpiece cover 108 is moved from the closed to the open position, the dose metering assembly of the inhaler 100 may prime a dose of medicament. In the illustrated example of FIG. 12, the mouthpiece cover 108 being moved from the closed to the open position may cause the bellows 112 to compress to deliver a dose of medication from the medication reservoir 110 to the dosing cup 116. Thereafter, a subject may inhale through the mouthpiece 106 in an effort to receive the dose of medication.

The airflow generated from the subject's inhalation may cause the deagglomerator 121 to aerosolize the dose of medication by breaking down the agglomerates of the medicament in the dose cup 116. The deagglomerator 121 may be configured to aerosolize the medication when the airflow through the flow pathway 119 meets or exceeds a particular rate, or is within a specific range. When aerosolized, the dose of medication may travel from the dosing cup 116, into the dosing chamber 117, through the flow pathway 119, and out of the mouthpiece 106 to the subject. If the airflow through the flow pathway 119 does not meet or exceed a particular rate, or is not within a specific range, the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, a single dose of medication may remain in the dosing cup until the dose has been aerosolized by the deagglomerator 121. When a dose of medication is delivered, a dose confirmation may be stored in memory at the inhaler 100 as dose confirmation information.

As the subject inhales through the mouthpiece 106, air may enter the air vent to provide a flow of air for delivery of the medication to the subject. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117. Further, the inhaler 100 may include a dose counter 111 that is configured to be initially set to a number of total doses of medication within the medication reservoir 110 and to decrease by one each time the mouthpiece cover 108 is moved from the closed position to the open position.

The top cap 102 may be attached to the main housing 104. For example, the top cap 102 may be attached to the main housing 104 through the use of one or more clips that engage recesses on the main housing 104. The top cap 102 may overlap a portion of the main housing 104 when connected, for example, such that a substantially pneumatic seal exists between the top cap 102 and the main housing 104.

Figure 14:
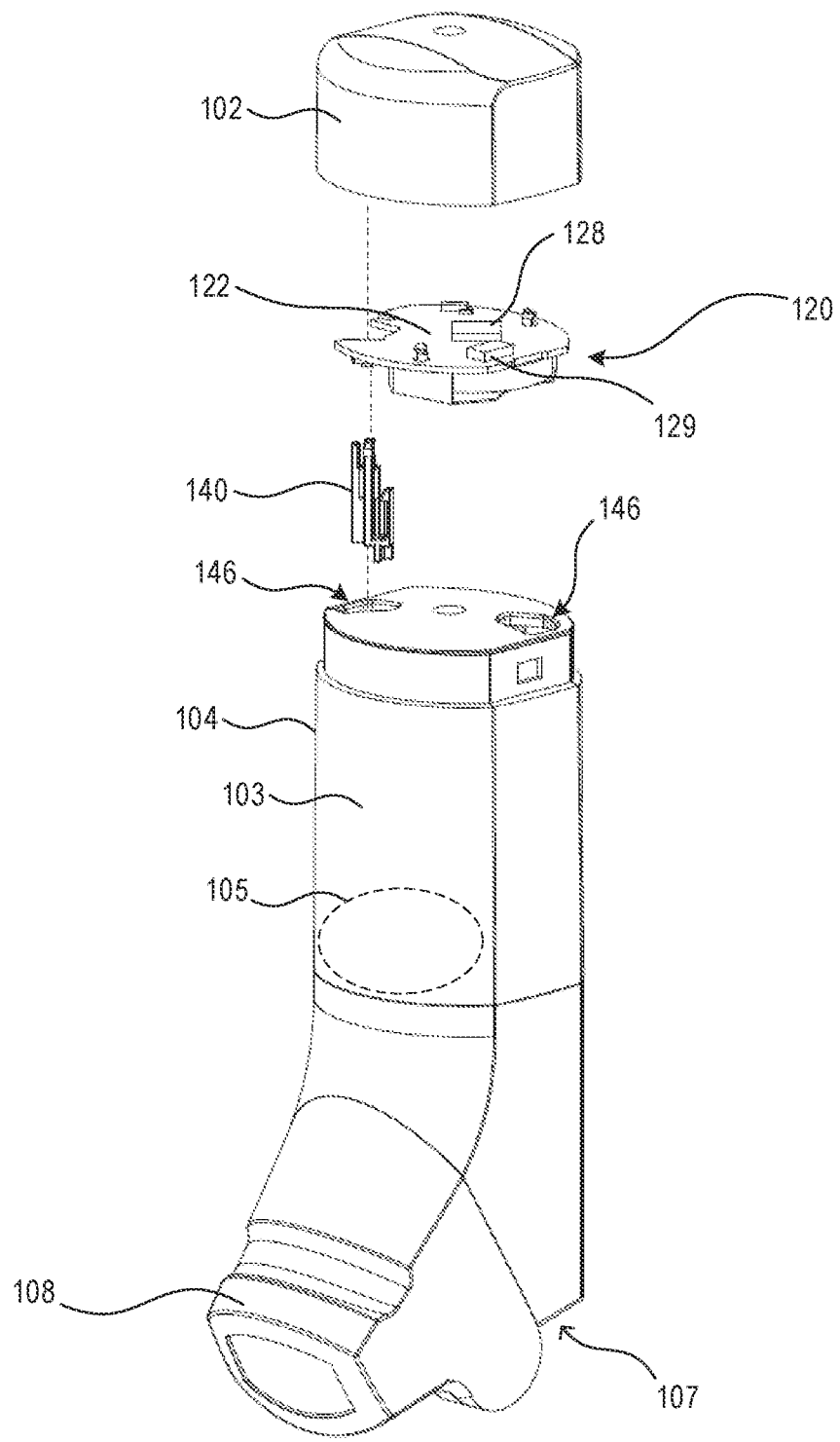
FIG. 14 is an exploded perspective view of the example inhaler shown in FIG. 12.

FIG. 14 is an exploded perspective view of the example inhaler 100 with the top cap 102 removed to expose the electronics module 120. As shown in FIG. 14, the top surface of the main housing 104 may include one or more (e.g. two) orifices 146. One of the orifices 146 may be configured to accept a slider 140. For example, when the top cap 102 is attached to the main housing 104, the slider 140 may protrude through the top surface of the main housing 104 via one of the orifices 146.

Figure 15:
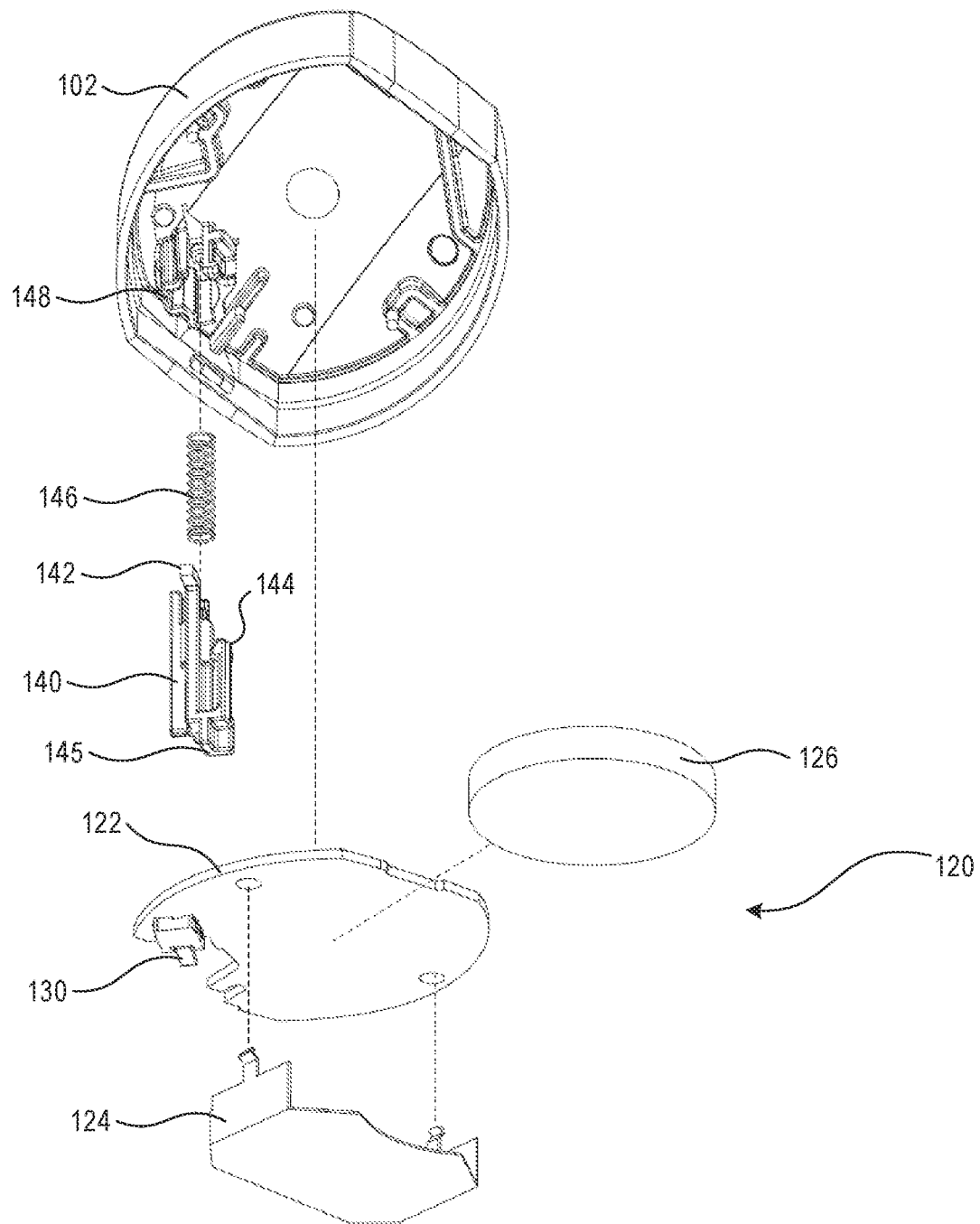
FIG. 15 is an exploded perspective view of a top cap and electronics module of the inhaler shown in FIG. 12.

FIG. 15 is an exploded perspective view of the top cap 102 and the electronics module 120 of the example inhaler 100. As shown in FIG. 21, the slider 140 may define an arm 142, a stopper 144, and a distal end 145. The distal end 145 may be a bottom portion of the slider 140. The distal end 145 of the slider 140 may be configured to abut the yoke that resides within the main housing 104 (e.g. when the mouthpiece cover 108 is in the closed or partially open position). The distal end 145 may be configured to abut a top surface of the yoke when the yoke is in any radial orientation. For example, the top surface of the yoke may include a plurality of apertures (not shown), and the distal end 145 of the slider 140 may be configured to abut the top surface of the yoke, for example, whether or not one of the apertures is in alignment with the slider 140.

The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g. abut) an upper portion (e.g. a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke when the mouthpiece cover 108 is closed. The distal end 145 of the slider 145 may also remain in contact with the yoke while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g. axial) travel of the slider 140. This limit may be less than the vertical travel of the yoke. Thus, as the mouthpiece cover 108 is moved to a fully open position, the yoke may continue to move in a vertical direction towards the mouthpiece 106 but the stopper 144 may stop the vertical travel of the slider 140 such that the distal end 145 of the slider 140 may no longer be in contact with the yoke.

More generally, the yoke may be mechanically connected to the mouthpiece cover 108 and configured to move to compress the bellows spring 114 as the mouthpiece cover 108 is opened from the closed position and then release the compressed bellows spring 114 when the mouthpiece cover reaches the fully open position, thereby causing the bellows 112 to deliver the dose from the medication reservoir 110 to the dosing cup 116. The yoke may be in contact with the slider 140 when the mouthpiece cover 108 is in the closed position. The slider 140 may be arranged to be moved by the yoke as the mouthpiece cover 108 is opened from the closed position and separated from the yoke when the mouthpiece cover 108 reaches the fully open position. This arrangement may be regarded as a non-limiting example of the previously described dose metering assembly, since opening the mouthpiece cover 108 causes the metering of the dose of the medicament.

The movement of the slider 140 during the dose metering may cause the slider 140 to engage and actuate a switch 130. The switch 130 may trigger the electronics module 120 to register the dose metering. The slider 140 and switch 130 together with the electronics module 120 may thus be regarded as being included in the use determination system 12 described above. The slider 140 may be regarded in this example as the means by which the use determination system 12 is configured to register the metering of the dose by the dose metering assembly, each metering being thereby indicative of the inhalation performed by the subject using the inhaler 100.

Actuation of the switch 130 by the slider 140 may also, for example, cause the electronics module 120 to transition from the first power state to a second power state, and to sense an inhalation by the subject from the mouthpiece 106.

The electronics module 120 may include a printed circuit board (PCB) assembly 122, a switch 130, a power supply (e.g. a battery 126), and/or a battery holder 124. The PCB assembly 122 may include surface mounted components, such as a sensor system 128, a wireless communication circuit 129, the switch 130, and or one or more indicators (not shown), such as one or more light emitting diodes (LEDs). The electronics module 120 may include a controller (e.g. a processor) and/or memory. The controller and/or memory may be physically distinct components of the PCB 122. Alternatively, the controller and memory may be part of another chipset mounted on the PCB 122, for example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field programmable gate array (FPGA), or any suitable processing device or control circuit.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smart phone.

The sensor system 128 may include one or more sensors. The sensor system 128 may be, for example, included in the use determination system 12 described above. The sensor system 128 may include one or more sensors, for example, of different types, such as, but not limited to one or more pressure sensors, temperature sensors, humidity sensors, orientation sensors, acoustic sensors, and/or optical sensors. The one or more pressure sensors may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous reading (e.g. pressure reading) to the controller of the electronics module 120 and/or aggregated readings (e.g. pressure readings) over time. As illustrated in FIGS. 13 and 14, the sensor system 128 may reside outside the flow pathway 119 of the inhaler 100, but may be pneumatically coupled to the flow pathway 119.

The controller of the electronics module 120 may receive signals corresponding to measurements from the sensor system 128. The controller may calculate or determine one or more airflow metrics using the signals received from the sensor system 128. The airflow metrics may be indicative of a profile of airflow through the flow pathway 119 of the inhaler 100. For example, if the sensor system 128 records a change in pressure of 0.3 kilopascals (kPa), the electronics module 120 may determine that the change corresponds to an airflow rate of approximately 45 liters per minute (Lpm) through the flow pathway 119.

Figure 16:
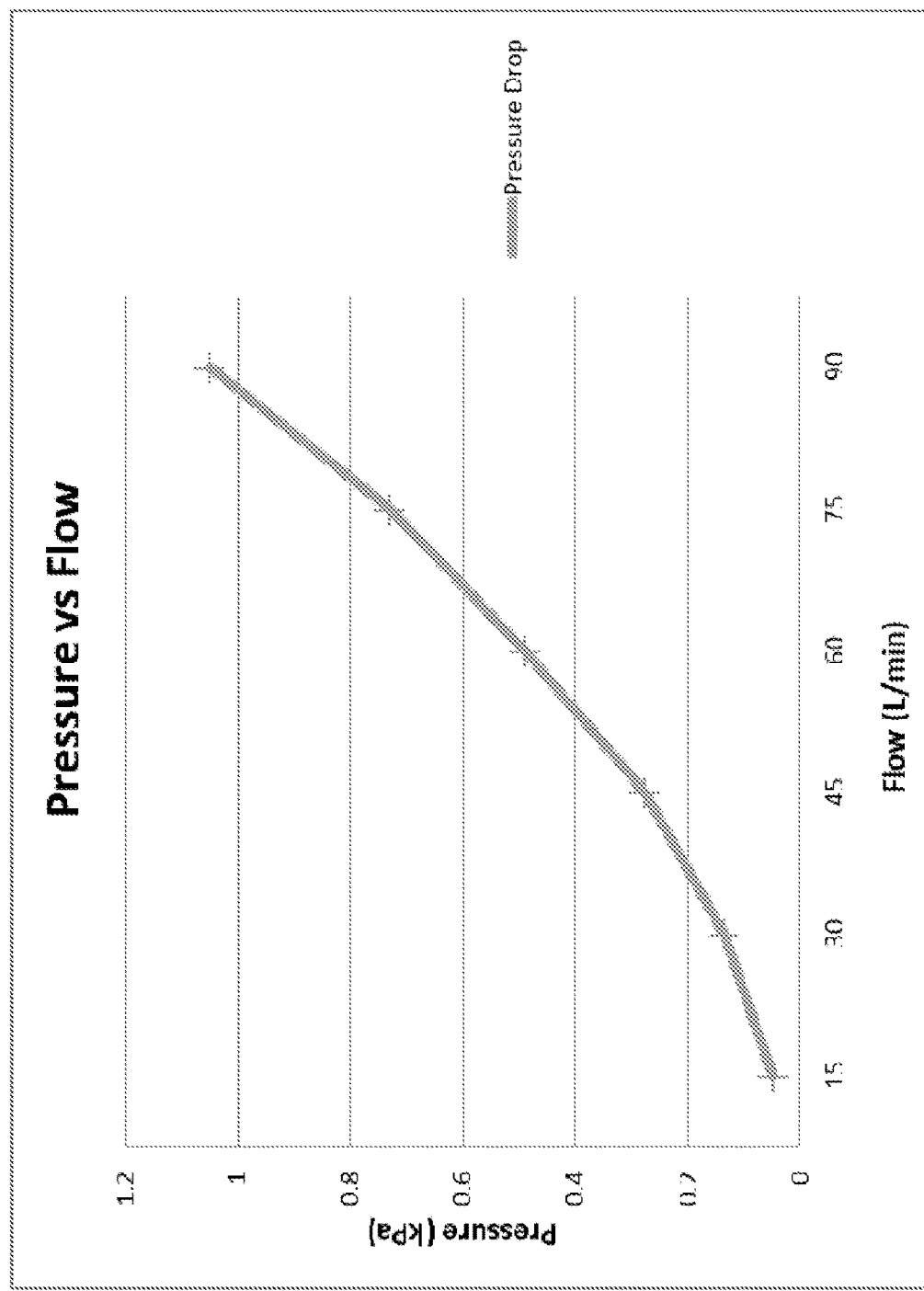
FIG. 16 is a graph of airflow rate through the example inhaler shown in FIG. 12 versus pressure.

FIG. 16 shows a graph of airflow rates versus pressure. The airflow rates and profile shown in FIG. 16 are merely examples and the determined rates may depend on the size, shape, and design of the inhalation device 100 and its components.

The processing module 34 may generate personalized data (e.g., usage events) in real-time by comparing signals received from the sensor system 128 and/or the determined airflow metrics to one or more thresholds or ranges, for example, as part of an assessment of how the inhaler 100 is being used and/or whether the use is likely to result in the delivery of a full dose of medication. For example, where the determined airflow metric corresponds to an inhalation with an airflow rate below a particular threshold, the processing module 34 may determine that there has been no inhalation or an insufficient inhalation from the mouthpiece 106 of the inhaler 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered.

The pressure measurement readings and/or the computed airflow metrics may be indicative of the quality or strength of inhalation from the inhaler 100. For example, when compared to a particular threshold or range of values, the readings and/or metrics may be used to categorize the inhalation as a certain type of event, such as a good inhalation event, a low inhalation event, a no inhalation event, or an excessive inhalation event. The categorization of the inhalation may be usage parameters stored as personalized data of the subject.

The no inhalation event may be associated with pressure measurement readings and/or airflow metrics below a particular threshold, such as an airflow rate less than or equal to 30 Lpm. The no inhalation event may occur when a subject does not inhale from the mouthpiece 106 after opening the mouthpiece cover 108 and during the measurement cycle. The no inhalation event may also occur when the subject's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

The low inhalation event may be associated with pressure measurement readings and/or airflow metrics within a particular range, such as an airflow rate greater than 30 Lpm and less than or equal to 45 Lpm. The low inhalation event may occur when the subject inhales from the mouthpiece 106 after opening the mouthpiece cover 108 and the subject's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate which is greater than 45 Lpm and less than or equal to 200 Lpm. The good inhalation event may occur when the subject inhales from the mouthpiece 106 after opening the mouthpiece cover 108 and the subject's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the subject's inspiratory effort exceeds the normal operational parameters of the inhaler 100. The excessive inhalation event may also occur if the device 100 is not properly positioned or held during use, even if the subject's inspiratory effort is within a normal range. For example, the computed airflow rate may exceed 200 Lpm if the air vent is blocked or obstructed (e.g. by a finger or thumb) while the subject is inhaling from the mouthpiece 106.

Any suitable thresholds or ranges may be used to categorize a particular event. Some or all of the events may be used. For example, the no inhalation event may be associated with an airflow rate which is less than or equal to 45 Lpm and the good inhalation event may be associated with an airflow rate which is greater than 45 Lpm and less than or equal to 200 Lpm. As such, the low inhalation event may not be used at all in some cases.

The pressure measurement readings and/or the computed airflow metrics may also be indicative of the direction of flow through the flow pathway 119 of the inhaler 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a subject is exhaling into the mouthpiece 106, which may signal that the subject is not using the device 100 properly.

The inhaler 100 may include a spirometer or similarly operating device to enable measurement of lung function metrics. For example, the inhaler 100 may perform measurements to obtain metrics related to a subject's lung capacity. The spirometer or similarly operating device may measure the volume of air inhaled and/or exhaled by the subject. The spirometer or similarly operating device may use pressure transducers, ultrasound, or a water gauge to detect the changes in the volume of air inhaled and/or exhaled.

The personalized data collected from, or calculated based on, the usage of the inhaler 100 (e.g. pressure metrics, airflow metrics, lung function metrics, dose confirmation information, etc.) may be computed and/or assessed via external devices as well (e.g. partially or entirely). More specifically, the wireless communication circuit 129 in the electronics module 120 may include a transmitter and/or receiver (e.g. a transceiver), as well as additional circuitry. The wireless communication circuit 129 may include, or define, the transmission module 14 of the inhaler 100.

For example, the wireless communication circuit 129 may include a Bluetooth chip set (e.g. a Bluetooth Low Energy chip set), a ZigBee chipset, a Thread chipset, etc. As such, the electronics module 120 may wirelessly provide the personalized data, such as pressure measurements, airflow metrics, lung function metrics, dose confirmation information, and/or other conditions related to usage of the inhaler 100, to an external processing module 34, such as a processing module 34 included in a smart phone 40. The personalized data may be provided in real time to the external device to enable exacerbation risk prediction based on real-time data from the inhaler 100 that indicates time of use, how the inhaler 100 is being used, and personalized data about the subject, such as real-time data related to the subject's lung function and/or medical treatment. The external device may include software for processing the received information and for providing compliance and adherence feedback to the subject via a graphical user interface (GUI). The graphical user interface may be included in, or may define, the user interface 38 included in the system 10.

The airflow metrics may include personalized data that is collected from the inhaler 100 in real-time, such as one or more of an average flow of an inhalation/exhalation, a peak flow of an inhalation/exhalation (e.g. a maximum inhalation received), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may re-zero to account for changes in atmospheric pressure before or after calculating the airflow metrics. The one or more pressure measurements and/or airflow metrics may be time-stamped and stored in the memory of the electronics module 120.

In addition to the airflow metrics, the inhaler 100, or another computing device, may use the airflow metrics to generate additional personalized data. For example, the controller of the electronics module 120 of the inhaler 100 may translate the airflow metrics into other metrics that indicate the subject's lung function and/or lung health that are understood to medical practitioners, such as peak inspiratory flow metrics, peak expiratory flow metrics, and/or forced expiratory volume in 1 second (FEV1), for example. The electronics module 120 of the inhaler may determine a measure of the subject's lung function and/or lung health using a mathematical model such as a regression model. The mathematical model may identify a correlation between the total volume of an inhalation and FEV1. The mathematical model may identify a correlation between peak inspiratory flow and FEV1. The mathematical model may identify a correlation between the total volume of an inhalation and peak expiratory flow. The mathematical model may identify a correlation between peak inspiratory flow and peak expiratory flow.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhaler 100 and/or the medication contained therein.

In a connected state, the communication circuit and memory may be powered on and the electronics module 120 may be "paired" with an external device, such as a smart phone. The controller may retrieve data from the memory and wirelessly transmit the data to the external device. The controller may retrieve and transmit the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

The data stored in the memory of the electronics module 120 (e.g. the signals generated by the switch 130, the pressure measurement readings taken by the sensory system 128 and/or the airflow metrics computed by the controller of the PCB 122) may be transmitted to an external device, which may process and analyze the data to determine the usage parameters associated with the inhaler 100. Further, a mobile application residing on the mobile device may generate feedback for the user based on data received from the electronics module 120. For example, the mobile application may generate daily, weekly, or monthly report, provide confirmation of error events or notifications, provide instructive feedback to the subject, and/or the like.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

What is claimed is:

1. A system for use with a plurality of medical inhalers, the system comprising:
   a plurality of electronics modules, where each electronics module is associated with an inhaler out of a plurality of inhalers, each inhaler comprising medicament, wherein the electronics module comprises a processor, memory, and a transmitter, wherein the processor of each the electronics module is configured to:
  determine usage events of the inhaler by a subject;
  assign a time to each usage event; and
  send data indicating the usage events and the time of the usage events; and
a digital health platform (DHP) comprising a transceiver, a memory, and a processor, wherein the processor of the DHP is configured to:
  receive data relating to each of a plurality of usage events of a plurality of users, each usage event relating to one of a plurality of inhalers, and each inhaler associated with a user out of the plurality of different users, wherein the data of each usage event comprises a time of the usage event and a medication type of the usage event;
  determine a medication type, a time of day, and a date range;
  determine a subset of the usage events based on the determined medication type, the determined time of day, and the determined date range;
  determine an inhalation count threshold;
  determine a number of usage events out of the subset of usage events that are associated with the same user and medication type;
  generate a prioritized filtered list of users out of the plurality of users based on a comparison of the inhalation count threshold with the number of usage events that are associated with the same user and medication type; and
  cause a display device to present a graphical user interface (GUI) that comprises the number of usage events for each user of the filtered list of users.

2. The system of claim 1, wherein the medication type comprises one or more rescue medication types and one or more maintenance medication types, and wherein the time of day comprises a start time and an end time or a selection for the entire day.

3. The system of claim 1, wherein the processor of the DHP, when generating the filtered list of users, is further configured to determine whether the number of usage events that are associated with the same user and medication type is greater than or less than the inhalation count threshold.

4. The system of claim 1, wherein the processor of the DHP, when generating the filtered list of users, is further configured to determine whether the number of usage events that are associated with the same user and medication type is proportionally smaller or greater than a count of a different, non-overlapping subset of the usage events that are associated with the same user and medication type.

5. The system of claim 4, wherein the different, non-overlapping subset of the usage events is associated with a different date range than the number of usage events, but is associated with the same medication type and time of day.

6. The system of claim 4, wherein the count of the different, non-overlapping subset of the usage events defines the inhalation count threshold.

7. The system of claim 1, wherein the plurality of usage events is associated with a program that defines the plurality of users and one or more medication types; and
  wherein the processor of the DHP is configured to store a filter based on the determined medication type, the determined time of day, the determined date range, and the inhalation count threshold, and associate the filter with the program so that the filter may be selected by a plurality of different heath care providers who are associated with an organization and the program.

8. The system of claim 7, wherein the processor of the DHP is configured to apply the filter to different programs associated with the organization.

9. The system of claim 7, wherein the processor of the DHP is configured to apply the filter to different programs associated with a different organization.

10. The system of claim 1, wherein the data of each usage event further comprises inhalation data;
  wherein the processor of the DHP is configured to determine a percentage of good inhalations for the number of usage events for each user of the filtered list, wherein the percentage of good inhalations comprises an indication of a percentage usage events out of the number of usage events where the associated inhalation data is above a threshold; and
  wherein the GUI further comprises an indication of the percentage of good inhalations for the number of usage events for each user of the filtered list.

11. The system of claim 10, wherein the inhalation data comprise a peak inspiratory flow (PIF) of the usage event.

12. The system of claim 1, wherein the processor of the DHP is further configured to:
  determine a last synchronization time for each of the plurality of inhalers, wherein the last synchronization time indicates the most recent time the inhaler was connected with an application residing on a user device; and
  wherein the GUI comprises an all-connected duration that indicates the last time that all of the inhalers of a particular medication type associated with a user have a confirmed connection between the inhaler and the application residing on the user device associated with the user regardless of whether a usage event was transferred during the connection.

13. The system of claim 12, wherein the all-connected duration indicates the oldest last synchronization time of the inhalers of the particular medication type associated with the user.

14. The system of claim 1, wherein the processor of the DHP is further configured to:
  determine a last synchronization time for each of the plurality of inhalers, wherein the last synchronization time indicates the most recent time the inhaler was connected with an application residing on a user device; and
  wherein the GUI comprises an all-connected duration that indicates the oldest last synchronization time of all of the inhalers of a particular medication type associated with a user that have a confirmed connection between the inhaler and the application residing on the user device associated with the user regardless of whether a usage event was transferred during the connection.

15. The system of claim 1, wherein the processor of the DHP is further configured to cause the display device to present the GUI with a listing of users that prioritizes users with an inhaler that has zero usage events and a confirmed connection between the inhaler and the application residing on the user device within a time frame over users with an inhaler that has zero usage events without a confirmed connection between the inhaler and the application residing on the user device within the time frame.

16. The system of claim 15, wherein the medicament type is a maintenance medicament type, and wherein the time frame is the last month or last 30 days.

17. The system of claim 1, wherein the processor of the DHP is configured to receive a selection from a user of one or more of the medication type, the time of day, or the date range.

18. The system of claim 17, wherein the processor of the DHP is configured to automatically determine one or more of medication type, the time of day, or the date range based on the user selection.

19. The system of claim 1, wherein the prioritized filtered list of users comprises no more than 30% of the plurality of users.

20. The system of claim 1, further comprising:
a plurality of mobile applications, wherein each mobile application is configured to:
connect to one or more electronics modules to receive the data indicating the usage events and the time of the usage events from the electronics modules;
determine one or more inhalation metrics based on the data indicating the usage events; and
send the data indicating the usage events, the time of the usage events, and the inhalation data to the DHP.

21. The system of claim 1, wherein the medicament comprises an inhaled corticosteroid (ICS) or a bronchodilator.

22. The system of claim 21, wherein the medicament is an ICS that comprises one or more of budesonide, beclomethasone (dipropionate), fluticasone (propionate), mometasone (furoate), ciclesonide, or dexamethasone (sodium).

23. The system of claim 21, wherein the medicament is a bronchodilator $\beta_2$-adrenergic agonist that comprises one or more of formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride), vilanterol (triphenylacetate), or albuterol (sulfate).

* * * * *